(12) United States Patent
Lewis et al.

(10) Patent No.: US 8,765,677 B2
(45) Date of Patent: Jul. 1, 2014

(54) OMEGA CONOTOXIN PEPTIDES

(75) Inventors: Richard Lewis, Wooloongabba (AU); David John Adams, Kew (AU); Geza Berecki, Glen Iris (AU); Roger Drinkwater, Vernon (CA); Paul Francis Alewood, Pullenvale (AU); MacDonald James Christie, Allawah (AU)

(73) Assignees: The University of Queensland, Queensland (AU); The University of Sydney, Sydney (AU)

( * ) Notice: Subject to any disclaimer, the term of this patent is extended or adjusted under 35 U.S.C. 154(b) by 0 days.

(21) Appl. No.: 13/497,363

(22) PCT Filed: Sep. 21, 2010

(86) PCT No.: PCT/AU2010/001228
§ 371 (c)(1),
(2), (4) Date: Sep. 5, 2012

(87) PCT Pub. No.: WO2011/032233
PCT Pub. Date: Mar. 24, 2011

(65) Prior Publication Data
US 2012/0329717 A1 Dec. 27, 2012

(30) Foreign Application Priority Data
Sep. 21, 2009 (AU) ................................ 2009904560

(51) Int. Cl.
*A61K 38/16* (2006.01)
*C07K 14/00* (2006.01)
*A61P 35/00* (2006.01)
*A61P 9/12* (2006.01)
*A61P 29/00* (2006.01)
*A61P 1/00* (2006.01)
*A61P 13/00* (2006.01)
*A61P 25/18* (2006.01)
*A61P 25/04* (2006.01)

(52) U.S. Cl.
USPC ........ 514/15.7; 530/324; 514/71.7; 514/21.3; 514/18.3; 435/375; 435/7.2

(58) Field of Classification Search
USPC ................. 530/324; 435/357, 7.21
IPC .............. A61P 13/10,1/00, 25/00, 25/04, 25/18, A61P 29/00, 9/12, 11/08; A61K 38/16, 38/17; C07K 14/00, 14/435; C12N 5/071; G01N 33/566
See application file for complete search history.

(56) References Cited

U.S. PATENT DOCUMENTS

| 4,569,967 A | 2/1986 | Kornreich et al. |
| 6,136,786 A | 10/2000 | Justice et al. |
| 7,101,849 B1 * | 9/2006 | Drinkwater et al. ......... 514/17.4 |
| 7,312,195 B2 | 12/2007 | Craik et al. |

FOREIGN PATENT DOCUMENTS

| AU | 2006236006 | 11/2006 |
| WO | WO 91/07980 | 6/1991 |
| WO | 02/07675 | 1/2002 |
| WO | 2008/088422 | 7/2008 |

OTHER PUBLICATIONS

G. Berecki, Analgesic w-Conotoxins CVIE and CVIF Selectively and Voltage-Dependently Block Recombinant and Native N-Type Calcium Channels, Molecular Pharmacology, Nov. 2009, vol. 77, pp. 139-148.*
Bettler et al. "Molecular structure and physiological functions of GABA(B) receptors," Physiol Rev, 84: 835-867, 2004.
Bowery et al. International Union of Pharmacology. XXXIII. Mammalian gamma-aminobutyric acid(B) receptors: structure and function, Pharmacol Rev, 54: 247-264, 2002.
Brock et al. "Relationship between the nerve action potential and transmitter release from sympathetic postganglionic nerve terminals," Nature, 326: 605-607, 1987.
Bures et al. "Determination of disulfide structure in agouti-related protein (AGRP) by stepwise reduction and alkylation," Biochemistry, 37:12172-12177, 1998.
Butler, Mammalian Cell Biotechnology: A Practical Approach, IRL Press, 1991.
Chaplan et al. "Quantitative assessment of tactile allodynia in the rat paw," J Neurosci Methods, 53: 55-63, 1994.
Cleland et al. "The development of stable protein formulations: a close look at protein aggregation, deamidation, and oxidation," Crit Rev Therap Drug Carr Syst, 10:307-377, 1993.
Ekberg et al. "muO-conotoxin MrVIB selectively blocks Nav1.8 sensory neuron specific sodium channels and chronic pain behavior without motor deficits," Proc Natl Acad Sci USA, 103: 17030-17035, 2006.
Flinn et al. "Synthesis and biological characterization of a series of analogues of omega-conotoxin GVIA," J Pept Sci, 1: 379-384, 1995.

(Continued)

*Primary Examiner* — Julie Ha
*Assistant Examiner* — Erinne Dabkowski
(74) *Attorney, Agent, or Firm* — Casimir Jones, S.C.

(57) ABSTRACT

This invention relates to an isolated, synthetic or recombinant peptide, wherein the peptide comprises the sequence: C K G K G A $Xaa_1$ C R $Xaa_2$ $Xaa_3$ $Xaa_4$ Y $Xaa_5$ C C $Xaa_6$ G $Xaa_7$ C R $Xaa_8$ $Xaa_9$ R C SEQ ID NO: 1 wherein $Xaa_1$, $Xaa_3$, $Xaa_4$, $Xaa_6$, $Xaa_7$ and $Xaa_8$ are independently selected from serine and threonine; $Xaa_2$ is selected from arginine and lysine; $Xaa_5$ is selected from aspartic acid and glutamic acid; and $Xaa_9$ is selected from glycine, alanine, valine, leucine and isoleucine.

15 Claims, 15 Drawing Sheets

(56) References Cited

OTHER PUBLICATIONS

Hamill et al. "Improved patch-clamp techniques for high-resolution current recording from cells and cell-free membrane patches," Pflugers Arch, 391: 85-100, 1981.

Hille et al. "Rate and Site of Action of Local Anesthetics in Myelinated Nerve Fibers," Molecular Mechanisms of Anesthesia, vol. 1: Prog in Anesthesiology, BR Fink (ed.) Raven Press, NY 13-20, 1975.

Hackeng et al. "Chemical synthesis of human protein S thrombin-sensitive module and first epidermal growth factor module," Biopolymers, 46: 53-63, 1998.

Lew et al. "Structure-function relationships of omega-conotoxin GVIA. Synthesis, structure, calcium channel binding, and functional assay of alanine-substituted analogues," J Biol Chem, 272: 12014-12023, 1997.

Lewis et al. "Novel omega-conotoxins from *Conus catus* discriminate among neuronal calcium channel subtypes," J Biol Chem, 275: 35335-35344, 2000.

Moffatt et al. "Approaches towards the quantitative analysis of peptides and proteins by reversed-phase high-performance liquid chromatography in the absence of a pure reference sample," J Chromatogr A, 891:235-242, 2000.

Motin et al. "Omega-conotoxin CVIB differentially inhibits native and recombinant N- and P/Q-type calcium channels," Eur J Neurosci, 25: 435-444, 2007.

Motin et al. "omega-Conotoxin inhibition of excitatory synaptic transmission evoked by dorsal root stimulation in rat superficial dorsal horn," Neuropharmacol, 55:860-864, 2008.

Mould et al. The alpha2delta auxiliary subunit reduces affinity of omega-conotoxins for recombinant N-type (Cav2.2) calcium channels, J Biol Chem, 279: 34705-34714, 2004.

Purves et al. Microelectrode methods for intracellular recording and ionophoresis, Academic Press, Harcourt Brace Jovanovich Publishers, 1991.

Sambrook et al. Molecular Cloning: A Laboratory Manual, Cold Spring Harbor Press, 1989.

Sato et al. "Active site of mu-conotoxin GIIIA, a peptide blocker of muscle sodium channels," J Biol Chem, 266: 16989-168991, 1991.

Schnolzer et al. "In situ neutralization in Boc-chemistry solid phase peptide synthesis. Rapid, high yield assembly of difficult sequences," Int J Pept Protein Res, 40: 180-193, 1992.

Scott et al. "Actions of intrathecal omega-conotoxins CVID, GVIA, MVIIA, and morphine in acute and neuropathic pain in the rat," Eur J Pharmacol, 451: 279-286, 2002.

Seltzer et al. "A novel behavioral model of neuropathic pain disorders produced in rats by partial sciatic nerve injury," Pain, 43: 205-218, 1990.

Smith et al. "Ryanodine-sensitive calcium stores involved in neurotransmitter release from sympathetic nerve terminals of the guinea-pig," J Physiol, 497(pt 3): 657-664, 1996.

Smith et al. "Multiple calcium channels control neurotransmitter release from rat postganglionic sympathetic nerve terminals," J Physiol, 499: 341-349, 1997.

Stocker et al. "Preferential interaction of omega-conotoxins with inactivated N-type Ca2+ channels," J Neurosci, 17: 3002-3013, 1997.

Yasuda et al. "Overexpressed Ca(v)beta3 inhibits N-type (Cav2.2) calcium channel currents through a hyperpolarizing shift of ultra-slow and closed-state inactivation," J Gen Physiol, 123: 401-416, 2004.

Database GenBank Accession No. AAF89878, "Four-Loop Conotoxin Precursor [*Conus catus*]" Duda, T.F. and Palumbi, S.R., Aug. 2, 1999, as accessed on Nov. 2, 2012 from http://www.ncbi.nlm.nih.gov/protein/AAF89878.

Duda et al. "Gene expression and feeding ecology: evolution of piscivory in the venomous gastropod genus *Conus*," Proc Biol Sci., 271(1544):1165-1174, 2004.

International Search Report and Written Opinion for PCT/AU2010/001228, mailed on Dec. 17, 2010.

Neumann et al. "Functional studies in atrium overexpressing A1-adenosine receptors," Br J Pharmacol, 128: 1623-1629, 1999.

Shon et al. "A noncompetitive peptide inhibitor of the nicotinic acetylcholine receptor from *Conus purpurascens* venom," Biochemistry, 36: 9581-9587, 1997.

\* cited by examiner

A

B

A

B

A

B

OMEGA CONOTOXIN PEPTIDES

This application is a §371 US National Entry of International Application No. PCT/AU2010/001228, filed Sep. 21, 2010, which is incorporated by reference herein in its entirety, and which claims the benefit Australian Patent Application No. 2009904560, filed Sep. 21, 2009.

The present invention relates to novel omega conotoxin (ω-conotoxin) peptides, their use as pharmacological tools and their use in any indication in which inhibition of N-type calcium channels may be of benefit, for example in reducing neuronal damage following ischemia, in the production of analgesia, in enhancing opiate analgesia, in modulating a drug related effect or behaviour, or in the treatment of pain, schizophrenia, stimulant induced psychoses, hypertension, inflammation, overactive bladder, non-inflammatory gastrointestinal disorders, or diseases which cause bronchoconstriction. The invention also relates to pharmaceutical compositions comprising these peptides.

Conotoxin peptides (conotoxins) typically contain 12-32 amino acids joined in a linear sequence. These peptides interfere with neurotransmission by targeting a variety of ion-channels or receptors and are found in the venom of marine snails of the genus *Conus* (cone snails), who are predators of fish, worms or other molluscs. The venom from any single *Conus* species may contain more than 100 different peptides.

Most conotoxin peptides contain either four (4) or six (6) cysteine residues, which are bonded in pairs to form either two (2) or three (3) disulfide bonds, respectively. ω-Conotoxins for example typically have from 24 to 32 amino acids with six characteristic cysteine substitutions and a pattern of disulfide bonds. The pattern of disulfide bonds and the distribution of the cysteine residues mean that ω-conotoxins can be considered to comprise four loops. These loops are between cysteine residues 1 and 2, 2 and 3, 4 and 5, and 5 and 6, as cysteine residues 3 and 4 are adjacent.

Conotoxins are divided into classes on the basis of their known physiological targets. ω-Conotoxins are one such class, and these peptides are known to target voltage-gated calcium channels (VGCCs), inhibiting neurotransmitter release. Studies of different ω-conotoxins, including both naturally occurring ω-conotoxins and synthetic variants, have illustrated that these peptides display varying affinity and selectivity for various subtypes of VGCCs. The affinity of a number of these ω-conotoxins for specific subtypes has made them important research tools.

An alphabetical nomenclature for subtypes of VGCCs has evolved for distinct classes of $Ca^{2+}$ currents, and these are divided into three main families and a number of subtypes. L-type VGCCs require a strong depolarisation for activation and are the main $Ca^{2+}$ currents recorded in muscle and endocrine cells, where they initiate contraction and secretion. N-type, P/Q-type and R-type VGCCs also require strong depolarisation for activation, but these subtypes are mostly found in neurons, where they initiate neurotransmission. T-type VGCCs are activated by weak depolarisations and are transient, and they are found in a wide variety of cell types.

VGCCs are multi-subunit complexes, which include the large pore-forming $\alpha_1$ subunit. Different calcium channel $\alpha_1$ subunits are found in different subtypes of VGCC. In particular, L-type VGCCs are represented by the $\alpha_{1C}$, $\alpha_{1D}$, $\alpha_{1F}$ and $\alpha_{1S}$ ($Ca_v$1.1-1.4) subunits. P/Q-type, N-type and R-type VGCCs are represented by $\alpha_{1A}$ ($Ca_v$2.1), $\alpha_{1B}$ ($Ca_v$2.2) and $\alpha_{1E}$ ($Ca_v$2.3) subunits, respectively. T-type VGCCs are formed by $\alpha_{1G}$, $\alpha_{1H}$ and $\alpha_{1I}$ subunits ($Ca_v$3.1-3.3, respectively).

Some ω-conotoxins, such as GVIA, MVIIA and CVID exhibit selectivity for N-type VGCCs. Other ω-conotoxins, such as MVIIC exhibit selectivity for P/Q-type VGCCs. The selectivity of a number of these peptides has led to the routine use of labelled forms of some of these peptides, such as $^{125}$I-GVIA, in pharmacological assays. New ω-conotoxins, which exhibit different binding profiles and affinities to different subtypes of VGCCs, may be useful in further defining subtypes of VGCCs.

In addition to their use as research tools, ω-conotoxins which target N-type calcium channels are useful as therapeutics. N-type VGCCs play important roles in regulating neuronal excitability and nociceptive transmission and are prominently involved in the transduction of acute and chronic pain perception. These channels represent important drug targets for the management of chronic and neuropathic pain and have been investigated in the development of new analgesic agents.

It has been suggested that ω-conotoxins with activity at N-type VGCCs may be useful as therapeutics for conditions including the reduction of neuronal damage following ischemia, in the production of analgesia, in enhancing opiate analgesia, in modulating a drug related effect or behaviour, or in the treatment of pain, schizophrenia, stimulant induced psychoses, hypertension, inflammation, overactive bladder, non-inflammatory gastrointestinal disorders, or diseases which cause bronchoconstriction. The compounds of the invention may be useful in any indication where inhibition of N-type calcium channels may be of benefit.

ω-Conotoxins that selectively inhibit N-type VGCCs include MVIIA and CVID. MVIIA (Prialt, SNX-111, Ziconotide) has been granted regulatory approval by a number of government bodies worldwide for the treatment of severe chronic pain associated with cancer, AIDS and neuropathies. Significantly, MVIIA does not induce tolerance and it also works in patients who no longer respond to opioid drugs. Other conotoxins, such as CVID, are currently in clinical trials and hold promise for the treatment of severe chronic pain in cancer patients.

Despite these advances many of the presently available compounds are not ideal therapeutics. The most serious-effect of MVIIA appears to be orthostatic hypotension, presumably resulting from blockage of N-type VGCCs on neurons that regulate blood pressure. In contrast, CVID appears to be more efficacious than MVIIA at reducing pain-related behaviour in animals and is less prone to causing side effects. Compared with MVIIA, CVID has a different selectivity profile at N-type calcium channel splice variants and is more selective for N-type over P/Q-type calcium channels than other ω-conotoxins. Selectivity for the N-type VGCC over the P/Q-type channel is important as it has been suggested that blockade of P/Q-type channels may lead to death.

Moreover in vitro, recovery of N-type channels from CVID or MVIIA block is incomplete, whereas GVIA dissociates very slowly from recombinant N-type VGCCs. This makes CVID, MVIIA and GVIA potentially less suitable as therapeutics. CVID, MVIIA and GVIA also cause irreversible inhibition of synaptic transmission between primary afferents and superficial dorsal horn neurons of rats. Conversely, the block by ω-conotoxin CVIB, an antagonist of both N- and P/Q-type VGCCs, has been shown to reversibly inhibit excitatory synaptic transmission in the spinal cord. Recovery from block may influence how effectively ω-conotoxins reverse different painful conditions in vivo, and could indicate whether administration of these peptides can be controlled to avoid unwanted side effects.

Accordingly there exists a need for new therapeutic agents which have selectivity for N-type VGCCs, favourable binding and reversibility characteristics at these channels, and which may be useful in the treatment of conditions related to N-type VGCCs.

In a first aspect of the present invention there is provided an isolated, synthetic or recombinant peptide, wherein the peptide comprises the sequence:

SEQ ID NO: 1
C K G K G A $Xaa_1$ C R $Xaa_2$ $Xaa_3$ $Xaa_4$ Y $Xaa_5$ C C $Xaa_6$ G $Xaa_7$ C R $Xaa_8$ $Xaa_9$ R C wherein
$Xaa_1$, $Xaa_3$, $Xaa_4$, $Xaa_6$, $Xaa_7$ and $Xaa_8$ are independently selected from serine and threonine;
$Xaa_2$ is selected from arginine and lysine;
$Xaa_5$ is selected from aspartic acid and glutamic acid; and
$Xaa_9$ is selected from glycine, alanine, valine, leucine and isoleucine.

In various embodiments, $Xaa_1$ to $Xaa_9$ are selected from a combination of one or more of the following:
$Xaa_1$ is serine;
$Xaa_2$ is selected from arginine and lysine;
$Xaa_3$ is threonine;
$Xaa_4$ is serine;
$Xaa_5$ is aspartic acid;
$Xaa_6$ is threonine;
$Xaa_7$ is serine;
$Xaa_8$ is serine; and
$Xaa_9$ is selected from glycine, alanine, valine, leucine and isoleucine.

In another embodiment, $Xaa_1$, $Xaa_4$, $Xaa_7$ and $Xaa_8$ are each serine. In a further embodiment, $Xaa_3$ and $Xaa_6$ are each threonine. In another embodiment, $Xaa_5$ is aspartic acid.

In one embodiment, $Xaa_2$ is arginine. In another embodiment, $Xaa_2$ is lysine.

In one embodiment of the invention, $Xaa_9$ is selected from glycine, alanine, leucine or isoleucine. $Xaa_9$ may be selected from glycine or alanine. $Xaa_9$ may also be selected from leucine or isoleucine.

In an embodiment of the invention, $Xaa_9$ is leucine. When $Xaa_2$ is arginine, $Xaa_9$ is leucine, $Xaa_1$, $Xaa_4$, $Xaa_7$ and $Xaa_8$ are each serine, $Xaa_3$ and $Xaa_6$ are each threonine, and $Xaa_5$ is aspartic acid, there is provided an isolated, synthetic or recombinant peptide designated as peptide 2, which comprises the sequence:

SEQ ID NO: 2
C K G K G A S C R R T S Y D C C T G S C R S L R C

When $Xaa_2$ is lysine, $Xaa_9$ is leucine, $Xaa_1$, $Xaa_4$, $Xaa_7$ and $Xaa_8$ are each serine, $Xaa_3$ and $Xaa_6$ are each threonine, and $Xaa_5$ is aspartic acid, there is provided an isolated, synthetic or recombinant peptide designated as peptide 3, which comprises the sequence:

SEQ ID NO: 3
C K G K G A S C R K T S Y D C C T G S C R S L R C

In another embodiment of the invention, $Xaa_9$ is glycine. When $Xaa_2$ is arginine, $Xaa_9$ is glycine, $Xaa_1$, $Xaa_4$, $Xaa_7$ and $Xaa_8$ are each serine, $Xaa_3$ and $Xaa_6$ are each threonine, and $Xaa_5$ is aspartic acid, there is provided an isolated, synthetic or recombinant peptide designated as CVIE, which comprises the sequence:

SEQ ID NO: 4
C K G K G A S C R R T S Y D C C T G S C R S G R C

When $Xaa_2$ is lysine, $Xaa_9$ is glycine, $Xaa_1$, $Xaa_4$, $Xaa_7$ and $Xaa_8$ are each serine, $Xaa_3$ and $Xaa_6$ are each threonine, and $Xaa_5$ is aspartic acid, there is provided an isolated, synthetic or recombinant peptide designated as [R10K]CVIE, which comprises the sequence:

SEQ ID NO: 5
C K G K G A S C R K T S Y D C C T G S C R S G R C

Advantageously, the peptides of the present invention may not include methionine. Methionine is present in other ω-conotoxins such as MVIIA, MVIIC, CVIB and CVID. Methionine residues are prone to oxidation, which can result in reduced purity, and loss of activity or selectivity in solution. This can pose particular problems in terms of storing the peptide over a long period of time, as is the case for formulated peptides delivered from a reservoir of a pumping device. Steps need to be undertaken in synthesising and formulating methionine-containing peptides to minimise this oxidation, complicating these processes.

In the sequences single letter codes have been used to denote different amino acids. In these sequences the code C, or cysteine, is used to denote both cysteine and selenocysteine. However, any selenocysteines in these sequences must be positioned so that when the peptide is oxidised a diselenide bond is produced between two selenocysteines.

The peptides of the present invention have at least six cysteine residues. Preferably, the peptides have only six cysteine residues. The six cysteine residues may be bonded in pairs to form three disulfide or diselenide bonds. In one embodiment, one or more of the cysteine-cysteine bonds form disulfide bonds. In another embodiment, the peptides of the present invention possess six cysteine residues bonded in pairs to form three disulfide bonds.

The most common disulfide connectivity for ω-conotoxins are between cysteine residues I and IV, II and V, and III and VI, where the six Roman numerals represent the six cysteine residues (numbered from the N-terminus). Preferably, this disulfide or diselenide connectivity is present in the peptides of the present invention. Consequently, in one embodiment the cysteine-cysteine disulfide bonds in SEQ ID NO: 1 are: C1-C16; C8-C20; and C15-C25, numbered from the N-terminus. However, other connectivities are also within the scope of the claims.

In one embodiment, one or more of the cysteine-cysteine bonds form diselenide bonds. In this embodiment, the sulphydryl groups of cysteine are replaced with selenium equivalents.

Despite the difference in chemical properties, substitution of cysteine with selenocysteine represents one of the most conservative substitutions that can be introduced into a peptide, since both exhibit very similar physical properties. The presence of two selenocysteine residues in a peptide chain allows the formation of a diselenide bond which is analogous to the disulfide bond. Disulfides and diselenides both exhibit similar bond geometry, with a diselenide exhibiting a slightly longer bond length due to the larger size of the selenium atom.

Disulfide bonds play an important role in the conformational stability of many naturally occurring peptide hormones and animal toxins. However, substitution of disulfides with diselenides may affect the properties of the compounds of the present invention. For instance, diselenide bonds would be expected to exhibit increased stability in a reducing environment, such as the cytosol due to the increased redox potential. As the mode of action of many drugs often occurs in a reducing environment, it would be expected that systematic replacement of cysteine with selenocysteine would result in increased stability.

Methods of preparing selenocysteine would be known to a person skilled in the art. One experimental protocol is outlined in U.S. Pat. No. 7,312,195. In this protocol β-chloro-alanine is added dropwise to a solution of sodium diselenide to produce selenocysteine.

Peptides containing an N- or C-terminal selenocysteine residue may possess similar properties to those containing a cysteine residue at these positions. For example, peptides containing an N-terminal selenocysteine will react with peptides containing a C-terminal thioester to form a selenoester intermediate under reducing conditions that spontaneously rearranges to give the more stable amide bond. Moreover, peptides possessing both an N-terminal selenocysteine and a C-terminal thioester can react to yield an N-to-C cyclic peptide, as will peptides that possess an N-terminal cysteine and a C-terminal thioester.

Additional amino acids or other substituents may be added to the N- or C-termini of the peptides of the present invention. For example, the peptides of the present invention may form part of a longer sequence, with additional amino acids added to either or both of the N- and C-termini. In another example, various non-peptide substituents may also be added to either or both of the N- and C-termini. Since such additional substituents do not necessarily bind to or occlude the primary target of the peptides of the present invention, the N- and C-termini may be modified to alter physicochemical properties, potentially reduce any side effects, or otherwise improve the therapeutic use of the peptide, such as by improving stability. In one example, modifications at the N- or C-termini may improve membrane penetration or solubility.

In one embodiment, a primary, secondary or tertiary amide or an ester may be present at the C-terminus of the peptides of the present invention. Preferably, the peptides are amidated or have a free carboxyl group at the C-terminus. More preferably, the peptides have a primary amide or a free carboxyl group at the C-terminus. More preferably, the peptides have a primary amide at the C-terminus.

Similarly, compounds with a substituted amine or substituted amide at the N-terminus are also considered to be within the scope of the present invention. Preferably, the N-terminus of the peptide is a primary amine, pyroglutamide or acetamide. More preferably, the N-terminus of the peptide is a primary amine.

In one embodiment, the C-terminus of the peptide is a primary amide and the N-terminus is unsubstituted.

The peptides of the present invention may also be attached to a solid support. This may be achieved by linking the sequence to the support via either the N- or C-termini. Various linkers, including peptidic linkers, may used to link the sequence to the solid support.

In a further embodiment, the C-terminus of the conotoxin peptide may be linked to the N-terminus by a linker, as described in Australian Patent Application No. 2006236006.

The N- and C-termini would generally be linked via a linking moiety, although in some cases it may be possible to directly connect the N- and C-termini of the conotoxin peptide without the need for such a linking moiety. The linking moiety, if present, may be a peptide linker such that cyclisation produces an amide-cyclised peptide backbone. These peptides will have no free N- or C-termini.

Considerable variation in the peptide sequence of this linking moiety is possible. Since this linking region does not necessarily bind to or occlude the primary active site of the peptides of the invention, the linking region can be modified to alter physiochemical properties, and potentially reduce side effects of the peptides, or otherwise improve the therapeutic use of the peptides, such as by improving stability.

The linking moiety will necessarily be of sufficient length to span the distance between the N- and C-termini of the conotoxin peptide. In the case of peptide linkers the length will generally be in the order of 2 to 10 amino acids. In some cases longer or shorter peptide linkers may be required. In one example, the linking moiety may be composed of glycine and/or alanine residues in addition to any amino acid residues already present in the linear peptide.

Therefore, according to one embodiment of the peptides of the present invention, the C-terminus of the peptide is a carboxyl group or a primary amide, or the C-terminus is linked to the N-terminus by a linker.

The peptides according to the present invention may be in the form of salts. The salts of the compounds of the invention are preferably pharmaceutically acceptable, but it will be appreciated that non-pharmaceutically acceptable salts also fall within the scope of the present invention, since these are useful as intermediates in the preparation of pharmaceutically acceptable salts or may be useful in some applications, such as probes or assays.

The pharmaceutically acceptable salts include acid addition salts, base addition salts, salts of pharmaceutically acceptable esters and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicyclic, sulfamic, or tartartic acids. The counter ion of quarternary amines and pyridiniums include chloride, bromide, iodide, sulfate, phosphate, methansulfonate, citrate, acetate, malonate, fumarate, sulfamate, and tartate. The base addition salts include but are not limited to salts such as sodium, potassium, calcium, lithium, magnesium, ammonium and alkylammonium. The salts may be made in a known manner, for example by treating the compound with an appropriate acid or base in the presence of a suitable solvent.

The peptides useful according to the invention may be in crystalline form and/or in the form of solvates (e.g. hydrates) and it is intended that all of these forms be within the scope of the present invention. The term "solvate" is a complex of variable stoichiometry formed by a solute (in this invention, a compound of the invention) and a solvent. Such solvents should not interfere with the biological activity of the solute. Methods of solvation are generally known within the art.

The compounds of the present invention may be used as pharmaceuticals. Accordingly, in another aspect the present invention provides a composition comprising a peptide according to the present invention, and a pharmaceutically acceptable carrier or diluent.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives, care should be taken to ensure that the activity of the peptide is not destroyed in the process and that the peptide is able to reach its site of action without being destroyed. In some circumstances it may be necessary to protect the peptide by means known in the art, such as, for example, micro encapsulation. Similarly the route of administration chosen should be such that the peptide reaches its site of action.

The pharmaceutical forms suitable for injectable use include sterile injectable solutions or dispersions, and sterile powders for the extemporaneous preparation of sterile injectable solutions. They should be stable under the conditions of manufacture and storage and may be preserved against reduction or oxidation and the contaminating action of microorganisms such as bacteria or fungi.

Those skilled in the art may readily determine appropriate formulations for the peptides of the present invention using conventional approaches. Identification of preferred pH ranges and suitable excipients, for example antioxidants, is routine in the art (see for example Cleland et al, 1993). Buffer systems are routinely used to provide pH values of a desired range and include carboxylic acid buffers for example acetate, citrate, lactate and succinate. A variety of antioxidants are available for such formulations including phenolic compounds such as BHT or vitamin E, reducing agents such as methionine or sulphite, and metal chelators such as EDTA.

The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmolality, for example, sugars or sodium chloride. Preferably, the formulation for injection will be isotonic with blood. Prolonged absorption of the injectable compositions can be brought about by the use in the compositions of agents delaying absorption, for example, aluminium monostearate and gelatin. Pharmaceutical forms suitable for injectable use may be delivered by any appropriate route including intravenous, intramuscular, intraperitoneal, subcutaneous, intracerebral, intrathecal and epidural injection or infusion. In one embodiment, the composition is for intraperitoneal, subcutaneous or intravenous administration, especially intraperitoneal or subcutaneous administration.

Sterile injectable solutions are prepared by incorporating the active compounds in the required amount in the appropriate solvent with various other ingredients such as those enumerated above, as required, followed by filtered sterilization. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

Other pharmaceutical forms include oral and enteral formulations of the present invention, in which the active peptide may be formulated with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal or sublingual tablets, troches, capsules, elixirs, suspensions, syrups, wafers, and the like. It will be appreciated that some of these oral formulation types, such as buccal and sublingual tablets, have the potential to avoid liver metabolism. However the peptides of the present invention may also be delivered to the stomach where liver metabolism is likely to be involved. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Liquid formulations may also be administered enterally via a stomach or oesophageal tube.

Enteral formulations may be prepared in the form of suppositories by mixing with appropriate bases, such as emulsifying bases or water-soluble bases. It is also possible, but not necessary, for the peptides of the present invention to be administered topically, intranasally, intravaginally, intraocularly and the like.

The present invention also extends to any other forms suitable for administration, for example topical application such as creams, lotions and gels, or compositions suitable for inhalation or intranasal delivery, for example solutions, dry powders, suspensions or emulsions. The present invention also extends to parenteral dosage forms, including those suitable for intravenous, subcutaneous, intramuscular, intrathecal, and intracerebral or epidural delivery.

The conotoxins useful according to the present invention may be administered by inhalation in the form of an aerosol spray from a pressurised dispenser or container, which contains a propellant such as carbon dioxide gas, dichlorodifluoromethane, nitrogen, propane or other suitable gas or combination of gases. The compounds may also be administered using a nebuliser.

Pharmaceutically acceptable vehicles and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate the compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically acceptable vehicle. The specification for the novel dosage unit forms of the invention are dictated by and directly dependent on (a) the unique characteristics of the active material and the particular therapeutic effect to be achieved, and (b) the limitations inherent in the art of compounding active materials for the treatment of disease in living subjects having a diseased condition in which bodily health is impaired as herein disclosed in detail.

As mentioned above the principal active ingredient is compounded for convenient and effective administration in effective amounts with a suitable pharmaceutically acceptable vehicle in dosage unit form. A unit dosage form can, for example, contain the principal active compound in amounts ranging from 0.25 µg to about 2000 mg. Expressed in proportions, the active compound is generally present in from about 0.25 µg to about 2000 mg/ml of carrier. In the case of compositions containing supplementary active ingredients, the dosages are determined by reference to the usual dose and manner of administration of the said ingredients.

In another aspect of the present invention there is provided a method of treating or preventing a disease or condition in respect of which inhibition of an N-type calcium channel is associated with effective treatment, comprising administering to a subject in need thereof an effective amount of a peptide of the present invention.

Preferably the subject is in need of such treatment, although the peptide may be administered in a prophylactic sense.

In a further aspect, the present invention provides a use of a peptide of the present invention in the manufacture of a medicament for the treatment of a condition or disease in respect of which inhibition of an N-type calcium channel is associated with effective treatment.

The diseases or conditions with which inhibition of an N-type calcium channel are associated with effective treatment include a wide range of conditions and diseases, such as the reduction of neuronal damage following ischemia, production of analgesia, enhancement of opiate analgesia, treatment of schizophrenia, stimulant induced psychoses, hypertension, inflammation and diseases which cause bronchoconstriction, and in the inhibition of progression of chronic and neuropathic pain. It has also been found that N-type VGCCs are involved in conditions including hyperalgesia and allodynia associated with neuropathic and inflammatory pain. Furthermore, blockage of N-type VGCCs may be useful in the treatment of acute, chronic, inflammatory and neuropathic pain, and breakthrough pain.

Other conditions that have been associated with inhibition of an N-type calcium channel include overactive bladder, modulation of a drug related effect or behaviour, non-inflammatory gastrointestinal disorders and prevention or treatment of retinal or optic nerve head damage resulting from acute traumatic or acute ischemic events. Gastrointestinal disorders may include, for example, hiatal hernias, strictures, esophageal webs, Schatzki's ring, esophageal diverticula, esophageal scleroderma, motor disorders of the esophagus, such as achalasia and diffuse esophageal spasm, and irritable bowel syndrome. Drug related effects or behaviours include, for example, effects from ethanol, cannabinoids and opioids, such as stimulant, sedative, hypnotic and ataxic effects and also drug reward.

In another aspect of the present invention there is provided a method for reducing neuronal damage following ischemia, for the production of analgesia, for enhancement of opiate analgesia, for modulation of a drug related effect or behaviour, or for the treatment of pain, schizophrenia, stimulant induced psychoses, hypertension, inflammation, overactive bladder, non-inflammatory gastrointestinal disorders, or diseases which cause bronchoconstriction, comprising administering to a subject in need thereof an effective amount of a peptide of the present invention.

The present invention also provides the use of a peptide of the present invention in the manufacture of a medicament for reducing neuronal damage following ischemia, for the production of analgesia, for enhancement of opiate analgesia, for modulation of a drug related effect or behaviour, or for the treatment of pain, schizophrenia, stimulant induced psychoses, hypertension, inflammation, overactive bladder, non-inflammatory gastrointestinal disorders, or diseases which cause bronchoconstriction.

In another aspect of the present invention there is provided a method of treating or preventing chronic or neuropathic pain comprising administering to a subject in need thereof an effective amount of a peptide according to the present invention. In a further aspect, the present invention provides a method for the treatment of neuropathic pain, inflammatory pain or breakthrough pain, comprising administering to a subject in need thereof an effective amount of a peptide according to the present invention.

In another aspect, the present invention provides a use of a peptide according to the present invention in the manufacture of a medicament for the treatment of chronic or neuropathic pain. In a further aspect there is provided a use of a peptide according to the present invention in the manufacture of a medicament for the treatment of neuropathic pain, inflammatory pain or breakthrough pain.

While the peptide according to the invention may be the sole active ingredient administered to the subject, the administration of other active ingredients with said peptide is within the scope of the invention. For example, the peptide could be administered with one or more therapeutic agents, including other VGCC agonists or antagonists.

In another aspect of the present invention there is provided a method for enhancing analgesia, comprising administering to a subject in need thereof an effective amount of a peptide according to the present invention in combination with an effective amount of compound that has analgesic activity. In a further aspect there is provided a use of a peptide according to the present invention in the manufacture of a medicament for enhancing analgesia, wherein the peptide is for administration with a compound that has analgesic activity.

Suitable compounds that have analgesic activity include morphine, gabapentin, a monoamine transporter inhibitor, Cymbalta® (duloxetine hydrochloride) or a non-steroidal anti-inflammatory drug (NSAID).

The peptides of the present invention may be administered by any appropriate route including intravenous, intracerebroventricular, intramuscular, intraperitoneal, subcutaneous, intracerebral, intrathecal and epidural administration, especially intravenous, intraperitoneal and subcutaneous administration.

In one embodiment, the peptides of the present invention are used in the treatment of pain. This includes inflammatory pain, neuropathic pain, and breakthrough pain. The peptides may be administered to target the central nervous system (for example by intrathecal, intracerebroventricular or intracerebral administration) or the peripheral nervous system (for example by subcutaneous, intraperitoneal or intravenous administration).

In a further aspect, the present invention provides a method of inhibiting an N-type calcium channel, comprising contacting the N-type calcium channel with a peptide according to the present invention. This method may be conducted in vitro or in vivo. In a preferred embodiment, the method is conducted in vitro. This method includes, but is not limited to, screening of compound libraries to identify compounds that bind to an N-type calcium channel, assays to determine the biological activity of compounds that bind to an N-type calcium channel, or experiments to investigate the physiology or pharmacology of the N-type calcium channel. This method may also result in the treatment or prophylaxis of conditions or diseases in animals, such as humans.

As used herein, inhibition of the N-type calcium channel includes selective inhibition of the N-type calcium channel, and selective inhibition of subunits of the N-type calcium channel.

As used herein, the term "N-type VGCC" or "N-type calcium channel" includes any subtype or subunit of the N-type VGCC. The term also relates to N-type VGCCs found naturally in microorganisms and animals, including in humans, and also recombinant and synthetic receptors.

Peptides according to the present invention have been shown to have selectivity for N-type VGCCs over P/Q-type VGCCs. At the concentrations tested, peptides of the present invention have been shown to have no effect at other types of VGCCs, including L-, R-, and T-type VGCCs. The terms "selective" and "selectivity" as used herein mean that the binding activity for a given concentration of the peptide at the N-type VGCC is typically greater than the binding activity at, for example, the P/Q-type VGCC. Those skilled in the art would be able to readily determine the selectivity of the peptides for these VGCCs using standard techniques.

Peptides of the present invention have also been shown to exhibit different binding and reversibility characteristics when different subunits are present in the N-type VGCC. This may result in peptides of the present invention having differing activities in different tissues and/or in conditions or disease states, potentially allowing greater selectivity in treatment. This is because variants of the N-type VGCC have been shown to exhibit different expression levels in various tissues and it has also been shown that subunits of the N-type VGCC may be upregulated in different conditions or disease states. For example, N-type calcium channels which comprise a $\beta_{2a}$ subunit are believed to be located supraspinally. Moreover, it has also been shown that a feature of neuropathic pain is the upregulation of the $\alpha_2\delta_1$ subunit that associates with VGCC in dorsal root ganglia.

Peptides of the present invention have been shown to be active at N-type calcium channels which comprise either a $\beta_{2a}$ subunit or a $\beta_3$ subunit. Following block of N-type calcium channels comprising a $\beta_3$ subunit with peptides of the present invention, it has been shown that recovery from block is voltage dependent, and occurs efficiently at a holding potential of −125 mV. On the other hand, following block of N-type calcium channels comprising a $\beta_{2a}$ subunit with peptides of the present invention, it has been shown that recovery from block occurs efficiently and completely at a holding potential of −80 mV. Accordingly, peptides of the present invention have been shown to reversibly block N-type calcium channels. In particular, peptides of the present invention exhibit voltage dependent dissociation from N-type VGCCs associated with the $\beta_3$ subunit, and voltage independent dissociation from N-type VGCCs associated with the $\beta_{2a}$ subunit.

The terms "reversible" and "reversibly" as used herein mean that following inhibition of the N-type VGCC, the N-type VGCC substantially returns to its state prior to inhibition. Those skilled in the art would readily be able to determine the reversibility of the peptides of the invention at the VGCCs using standard techniques. Such techniques are outlined, for example, in Example 4.

Without wishing to be bound by theory, it is believed that the voltage-dependent block of N-type calcium channels comprising a $\beta_3$ subunit allows peptides of the present invention to be locked to or released from the site of interaction depending on the gating state of the channel.

Furthermore, and without wishing to be bound by theory, it is believed that some side effects associated with other ω-conotoxins may result from the incomplete recovery of N-type calcium channels comprising a $\omega_{2a}$ subunit following binding with these ω-conotoxins. In this regard, it has been found that recovery of N-type VGCCs from block by CVID and MVIIA are not affected by auxiliary β subunits, and recovery of N-type channels from CVID or MVIIA block is incomplete at −80 mV. In contrast, and as outlined above, peptides of the present invention exhibit efficient recovery from block at N-type calcium channels comprising a $\beta_{2a}$ subunit at −80 mV. This may explain why peptides of the present invention, and other ω-conotoxins, completely relieve mechanical allodynia in a nerve injury model of neuropathic pain, but the peptides of the present invention exhibit fewer side effects in this model than other ω-conotoxins as they have improved reversibility at cell membrane potentials in the physiological range of around −80 mV.

The present invention also extends to the use of the peptides of the invention in assays and screens to identify compounds with activity at N-type VGCCs. In such assays and screens, the peptides of the present invention may be unlabelled or may include a radioactive or fluorescent label.

In one aspect, the present invention provides a method of assaying a compound for its ability to bind to an N-type calcium channel, comprising the steps of: a) incubating the N-type calcium channel with a peptide according to the present invention in the presence of the compound; and b) detecting displacement of the binding of the peptide to the N-type calcium channel, wherein displacement of the binding is indicative of a compound that binds to the N-type calcium channel.

The term "incubating" refers to mixing or combining said conotoxin peptide, said compound and said N-type calcium channel in a solution. This may be at room temperature, or at lower or higher temperatures than room temperature. In one embodiment, the solution may be a buffered solution designed to promote binding. The solution may or may not be agitated. The solution may also be applied in a static manner or a continuous perfusion.

As used herein, a compound is taken to bind to an N-type calcium channel when an interaction between the compound and the channel can be determined by a person skilled in the art. In this context, "interact" or variants thereof, such as "interacting" or "interaction, is used in the broadest sense, including interaction at calcium channel binding site, allosteric interaction, and also interaction at one or more subunits of the N-type calcium channel. Preferably, this interaction would be sufficient to inhibit the receptor.

As used herein, "displacement" of the binding only refers to the method by which binding is determined, and does not limit or have any bearing on how the conotoxin peptide and the compound interact with the calcium channel. For example, the displacement of the binding of the conotoxin peptide to the calcium channel may be calculated by comparing the binding of the conotoxin peptide to the calcium channel in the presence of the compound, relative to the binding in the absence of the compound. A lower amount of binding in the presence of the compound is indicative of a compound that binds to the calcium channel.

Accordingly, in another aspect the present invention provides a method of testing the N-type calcium channel binding activity of a test peptide or compound, comprising (1) determining the level of binding of a peptide according to the present invention to N-type calcium channels in the absence of said test peptide or compound, (2) determining the level of binding of said peptide of the invention to N-type calcium channels in the presence of said test peptide or compound, and (3) comparing the level determined in step (1) to the level determined in step (2).

In a further aspect, the present invention provides a method of screening for identifying compounds which bind to N-type calcium channels, comprising (1) determining the level of binding of a peptide according to the present invention to N-type calcium channels in the absence of a test compound, (2) determining the level of binding of said peptide of the invention to N-type calcium channels in the presence of said test compound, and (3) comparing the level determined in step (1) to the level determined in step (2), thereby identifying compounds which bind to N-type calcium channels.

In a further aspect, there is provided a method of identifying a selective inhibitor of N-type VGCCs that may produce reduced side effects compared to MVIIA following administration to a subject in need thereof, the method comprising assaying the selective inhibitor for its ability to provide: (i) voltage independent reversible inhibition of N-type VGCCs comprising a $\beta_{2a}$ subunit; and (ii) voltage dependent reversible inhibition of N-type VGCCs comprising a $\beta_3$ subunit, wherein a selective inhibitor providing (i) and (ii) indicates reduced side effects following administration. Side effects may include those recited in Example 7. Compounds which exhibit>50% reversibility, and more preferably>80% reversibility, are preferred. Preferably such assays are performed in oocytes, and the reduced side effects are observed in animal models of disease. Preferably the compound is a conotoxin peptide, and more preferably the compound is a ω-conotoxin peptide.

Through these methods, compounds that bind to N-type calcium channels may be identified, and/or the activity of these compounds determined. The compounds to be tested could be produced synthetically, or through biological processes. Mixtures of compounds may also be tested, which may, for example, include testing of crude cone snail venom or extracts thereof. These compounds may be used as, or used to develop, new pharmaceuticals that target N-type calcium channels. For example, new pharmaceuticals may be developed through identifying new lead compounds or through studying the binding interaction between the peptides of the present invention and N-type calcium channels.

The peptides of the present invention may be used, possibly in a labelled from such as radiolabelled CVIE or CVIF, to run assays and/or screens to identify compounds which interact with N-type calcium channels and/or particular subunits of such channels. Those skilled in the art could readily establish such assays and/or screens.

Accordingly, a further embodiment the present invention provides a peptide of the present invention wherein at least one of the amino acids incorporates a radiolabel. Radiolabels may include, for example, $^{125}I$, $^{131}I$, $^{14}C$, $^{15}N$, $^{35}S$ or $^{3}H$. If $^{125}I$ is used, for example, the iodine could be attached to tyrosine or another appropriate reside. If no such residue exists, an amino acid incorporation/substitution scan could be conducted to establish a suitable location to incorporate/substitute such a residue. In other examples, within the peptide one or more hydrogens may be replaced with $^{125}I$, $^{131}I$ or $^{3}H$; one or more carbons may be replaced with $^{14}C$; or one or more nitrogens may be replaced with $^{15}N$. A variety of labelled versions of the compounds of the present invention may be readily prepared by standard methods and assessed for retention of their ability to bind to N-type VGCCs in standard assays. Labelled versions of the compounds which do retain the ability to bind to N-type VGCCs or binding portions of such channels could then be used in assays and/or screens.

Radioligand binding assays may be performed using N-type calcium channels and the labelled conotoxin peptide. The calcium channel may be incubated with the labelled peptide and the compound to be tested for activity at the N-type calcium channel. In one embodiment, these components are prepared for use as separate solutions of known concentrations. After binding is complete, the calcium channel is separated from the labelled peptide and the compound, such as through filtration. The amount of binding that has occurred is then determined and/or binding is then detected.

Non-specific binding may be determined by incubating the calcium channel with an excess of the unlabelled conotoxin peptide in the presence of the labelled peptide. For example, if labelled CVIE was used in the assay, then unlabelled CVIE would be used to determine non-specific binding. After incubation, the assay is conducted in the same manner as above. Non specific binding should be subtracted from total binding when calculating the specific binding for each compound tested. If necessary, other steps such as washing, filtering, shaking and stirring may be included in the assay procedure as necessary. Normally, wash steps are included following separation of the membrane-bound compound from the compound remaining in solution to enable quantification of the amount of compound that has bound (e.g. such as by counting a radioactive isotope). Specific binding is compared with the binding obtained when the calcium channel is incubated in the presence of the labelled peptide alone to determine the extent to which the test compound has displaced the labelled peptide.

Care should be taken to avoid artefacts when performing these assays. Such artefacts could make it appear that the compound to be tested binds to the calcium channel when it does not, or vice versa. For example, a buffer solution should be chosen for the assay that does not affect the binding of the compounds to the calcium channel. Similarly, preparations of test compounds should not have proteolytic activity. It is also desirable that the compounds that are identified to bind to the calcium channel are examined in a sufficient concentration range to enable a Scatchard analysis on the results. This type of analysis is well known in the art and can be assisted using computer programs.

Fluorescent labels may also be incorporated into peptides of the present invention. Fluorescent labelling compounds may include: cyanine 3 (Cy3), cyanine 5 (Cy5), 4,4-difluoro-4-bora-3a,4a-diaza-s-indacene (BODIPY), nitrobenzoxadiazole (NBD), 4-nitro-O-phenylenediamine (NPD), fluorescein, fluorescein isothiocyanate, rhodamine, methylrhodamine, tetramethylrhodamine, phycoerythrin, phycocyanin, allophycocyanin, o-phthaldehyde and fluorescamine. Fluorescent streptavidin may also be used in conjunction with biotin. Such fluorescent labels may be incorporated at the N- or C-terminus of the peptides of the present invention, or may be incorporated in selected loops of these peptides. For example, the labels may be attached through an existing chemically reactive amino acid, at a position that does not have a substantial adverse effect on binding between the peptide and the VGCC.

Therefore, according to a further embodiment of the peptides of the present invention, at least one of the amino acids in the peptide incorporates a radiolabel or a fluorescent label.

The methods may also include electrophysiological studies, such as patch clamp, intracellular recording and extracellular recording studies (Purves 1991; Brock and Cunnane 1987; Smith and Cunnane 1997; Hamill et al., 1981). In such studies membrane potential, whole cell and single channel currents may be measured, providing information on neurotransmitter release from nerve terminals and changes in ionic currents and membrane potential. The studies can be carried out on the following cells which include, but are not limited to, *Xenopus* oocytes, cultured neurones such as sensory neurones (e.g. dorsal root ganglia), parasympathetic neurones (e.g. submandibular and intracardiac ganglia), sympathetic neurones (e.g. pelvic ganglia) and central neurones. The studies can also be carried out on whole nerve preparations such as CNS or peripheral ganglion preparations, or peripheral neuro-effector tissues, including, but not limited to, guinea pig vas deferens, rat anococcygeus, guinea pig ileum, rat bladder, mammalian colon, mammalian artery, mammalian atria and rat trachea. For example, a candidate compound-evoked change in calcium current in a cell may be measured compared to a control when the cell is electrically stimulated.

The VGCC may be activated using a technique suitable for the assay or screen being performed. For cell based assays this may be achieved by depolarising the membrane, such as by applying a high concentration of potassium ions or by applying a current across the membrane. A cell can be depolarised by changing extracellular potassium concentration in the physiological salt solution that is bathing the cell. For example normal potassium concentration in a physiological salt solution is 4.0 to 5.0 mM (preferably, around 4.5-4.7 mM). Increasing the potassium concentration above 5 mM will start to depolarise the cell. Increasing the concentration above 20 mM to 150 mM will most certainly depolarise the cell, with maximum depolarisation being evoked by 150 mM. For organ based assays field stimulation would be required to activate the voltage-dependent calcium channels (Smith and Cunnane 1997; Smith and Cunnane 1996).

When measuring candidate compound-evoked changes in calcium channel current, the channel must be stimulated in order to observe an effect. The frequency of stimulation is important to observe the inhibition of the calcium channel current. For example pulses of 2 to 20 Hz at 2 to 10 second intervals for approximately 1 to 20 minutes can be used. Such frequencies would be used in tissue bath studies and intracellular and extracellular recording from smooth muscle cells or postganglionic nerves or preparations such as brain slices. If the duration of the stimulus (depolarising pulse) is too brief and infrequent then no inhibition is observed. On the other hand, if either the duration of the stimulus (depolarising pulse) or frequency is increased then the effect of inhibiting the calcium channel current is enhanced.

The rate of block of the calcium channel current in the presence of a test peptide or compound may be increased with higher frequencies of stimulation (depolarising pulses) such as may occur in intense pain. In conducting such assays and screens the frequency of activation of the calcium channels should preferably be greater than or equal to 0.1 Hz. The method of activation of VGCCs is by applying a depolarising voltage step from −80 mV to 0 mV. Both the duration of the voltage step (or pulse) and frequency of applying the voltage step influence the rate of inhibition (block) of the calcium current in the presence of the test peptide or compound, whereby increasing either the duration or frequency increase the rate of block analogous to the use-dependent block by local anaesthetics of voltage-dependent sodium channels (see Hile et al. 1975).

In another embodiment, the methods may include tissue or organ bath studies. Nerve-evoked contraction or relaxation of muscle may be measured in the presence and absence of conotoxin peptides to investigate whether the conotoxin can inhibit tissue contraction or relaxation (Neumann et al. 1999; Bettler et al. 2004; Bowery et al. 2002). Suitable tissues for such studies include: ileum, arteries, bladder, anococcygeus, atria, ventricular muscle, vas deferens, diaphragm, trachea and colon.

The methods may also include other assays as described in the Examples, including in vivo assays on rats such in Example 7.

In some of the methods discussed above, it may be necessary to produce a recombinant calcium channel. To produce a recombinant calcium channel, the DNA sequence for the calcium channel may be obtained and then incorporated into an expression vector with an appropriate promoter. Once the expression vector is constructed, it may then be introduced into the appropriate cell line using methods including $CaCl_2$, $CaPO_4$, microinjection, electroporation, liposomal transfer, viral transfer or particle mediated gene transfer.

The host cell may comprise prokaryote, yeast or higher eukaryote cells. Suitable prokaryotes may include, but are not limited to, eubacteria, such as Gram-negative or Gram-positive organisms, including Enterobacteriaceae. Such Enterobacteriaceae may include Bacilli (e.g. *B. subtilis* and *B. licheniformis*), *Escherichia* (e.g. *E. coli*), *Enterobacter*, *Erwinia*, *Klebsiella*, *Proteus*, *Pseudomonas* (e.g. *P. aeruginosa*), *Salmonella* (e.g. *Salmonella typhimurium*), *Serratia* (e.g. *Serratia marcescens*), *Shigella*, and *Streptomyces*. Suitable eukaryotic microbes include, but are not limited to, *Candida*, *Kluyveromyces* (e.g. *K. lactis*, *K. fragilis*, *K. bulgaricus*, *K. wickeramii*, *K. waltii*, *K. drosophilarum*, *K. thermotolerans* and *K. marxianus*), *Neurospora crassa*, *Pichia pastoris*, *Trichoderma reesia*, *Saccharomyces cerevisiae*, *Schizosaccharomyces pombe*, *Schwanniomyces* (e.g. *Schwanniomyces occidentalis*), and filamentous fungi (e.g. *Neurospora*, *Penicillium*, *Tolypocladium*, and *Aspergillus* (e.g. *A. nidulans* and *A. niger*)) and methylotrophic yeasts (e.g. *Hansenula*, *Candida*, *Kloeckera*, *Pichia*, *Saccharomyces*, *Torulopsis*, and *Rhodotorula*). Suitable multicellular organisms include, but are not limited to, invertebrate cells (e.g. insect cells including *Drosophila* and *Spodoptera*), plant cells, and mammalian cell lines (e.g. Chinese hamster ovary (CHO cells), monkey kidney line, human embryonic kidney line, mouse sertoli cells, human lung cells, human liver cells and mouse mammary tumor cells). An appropriate host cell can be selected without undue experimentation by a person skilled in the art.

The cell line may then be cultured in conventional nutrient media modified for inducing promoters, selecting transformants, or amplifying the genes encoding the desired sequences. Culture conditions, such as media, temperature, pH, and the like, can be selected without undue experimentation by the person skilled in the art (for general principles, protocols and practical techniques, see Butler, M. 1991; Sambrook 1989). The cells may then be selected and assayed for the expression of the calcium channel using standard procedures.

Unless stated otherwise, any assays on these receptors may be performed in vivo or in vitro. If calcium channels for said assays are produced through cellular processes, either intact cells or membranes prepared for the cells may be used.

The peptides according to the present invention may be prepared using standard peptide synthetic methods followed by oxidative disulfide bond formation, for example as discussed in Example 2. For example, the linear peptides may be synthesised by solid phase methodology using BOC chemistry, as described by Schnolzer et al., 1992. Following deprotection and cleavage from the solid support the reduced peptides are purified using preparative chromatography. The purified reduced peptides are oxidised in buffered systems. The oxidised peptides are purified using preparative chromatography. Reduction/alkylation techniques can be used to determine the disulfide bond connectivities using well documented procedures (Shon et al. 1997; Bures et al. 1998). The peptides can also be made using selective oxidative disulfide bond formation using the procedures outlined in Kent et al. 1998. General references describing the synthesis of conotoxins include Sato et al. 1991; Lew et al. 1997; Flinn et al. 1995 and WO 91/07980.

If an unsubstituted amide is desired at the C-terminus of the peptide, BHA or MBHA resin is preferred, as these resins provide the unsubstituted amide directly on cleavage. If N-methylamide is desired at the C-terminus of the peptide, then N-methyl BHA resin may be used. Should other N-substituted amides be desired, then techniques such as those disclosed in U.S. Pat. No. 4,569,967 may be followed, or alternatively it may be preferable to functionalise the C-terminus via solution phase methods.

Alternatively, it may be desired to link the C-terminus of the conotoxin peptide to the N-terminus by a linker. There are several ways in which linear conotoxins may be cyclised, for example as outlined in Australian Patent Application No. 2006236006.

In a first approach, an extended linear peptide is first synthesised "on resin" using solid phase peptide synthesis methods. This extended linear peptide comprises the native sequence starting at a cysteine residue at, or closest to, the N-teiminus and a C-terminal extension comprises the new linking moiety. Solid phase peptide synthesis may be synthesised using BOC chemistry, as described by Schnolzer et al., 1992. In another embodiment, Fmoc chemistry may be used. Following deprotection and cleavage, the extended conotoxin peptide is cyclised to a thioester intermediate which subsequently rearranges to an amine-cyclised peptide. This reduced peptide is then oxidised to form the disulfide bonds.

In another approach, the peptide is assembled using solid phase peptide synthesis methods as before. The additional residues may be added at the N- and/or C-termini, and following synthesis the peptide is deprotected and cleaved from resin. Preferably in this embodiment the N- and C-termini of the synthesised peptide are glycine residues. The peptide is then folded. Following cyclisation the N- and C-temini are coupled together. However, this approach may be complicated if large numbers of lysine, glutamic acid or aspartic acid residues are present in the sequence.

A third approach is to begin with an oxidised, mature conotoxin. A peptide linker may then be synthesised and ligated with the conotoxin using published procedures for the ligation of peptides. The extended peptide is then cyclised.

Other approaches are also possible, provided that the product is a cyclised conotoxin peptide having the required disulfide bonds. For example, the peptide may be synthesised using solution phase methods, or selective deprotection of cysteine residues may be employed.

The peptides of the present invention may also be prepared using recombinant DNA technology. A nucleotide sequence encoding the desired peptide sequence may be inserted into a suitable vector and protein expressed in an appropriate expression system, as previously discussed for recombinant calcium channels. In some instances, further chemical modification of the expressed peptide may be appropriate, for example C-terminal amidation. Under some circumstances it may be desirable to undertake oxidative bond formation of the expressed peptide as a chemical step following peptide expression. This may be preceded by a reductive step to provide the unfolded peptide. Those skilled in the art may readily determine appropriate conditions for the reduction and oxidation of the peptide.

In a further aspect the present invention provides an isolated nucleic acid molecule comprising a sequence of nucleotides encoding or complementary to a sequence encoding a peptide according to the present invention.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolate form, they may be integrated into or ligated to or otherwise fused or associated with other genetic molecules such as vector molecules and in particular expression vector molecules, such as those discussed above.

In a further aspect, the present invention contemplates a genetic construct comprising a nucleic acid capable of encoding a peptide according to the present invention. Preferably, the nucleic acid portion is operably linked to a promoter, such that the promoter is capable of directing expression of the nucleic acid in an appropriate cell.

In another aspect the present invention provides a nucleic acid probe comprising a sequence of nucleotides encoding or complementary to a sequence encoding all or part of a peptide according to the present invention.

As used herein a reference to a "probe" includes reference to a primer used in amplification or a probe for use in direct hybridization.

Still another aspect of the present invention relates to a monoclonal or polyclonal antibody to a peptide according to the present invention. Such antibodies may be selected from naturally occurring antibodies to the peptides of the present invention or may be specifically raised to the peptides using standard techniques. In the case of the latter, the peptides may first need to be associated with a carrier molecule. The antibodies of the present invention may be particularly useful as therapeutic or diagnostic agents.

In this regard, specific antibodies can be used to screen for the peptides according to the invention. Techniques for such assays are well known in the art and include, for example, sandwich assays and ELISA. Knowledge of peptide levels may be important for monitoring certain therapeutic protocols.

Certain embodiments of the invention will now be described with reference to the following examples which are intended for the purpose of illustration only and are not intended to limit the scope of the generality hereinbefore described.

REFERRING TO THE FIGURES

EXAMPLES

Figure 1:
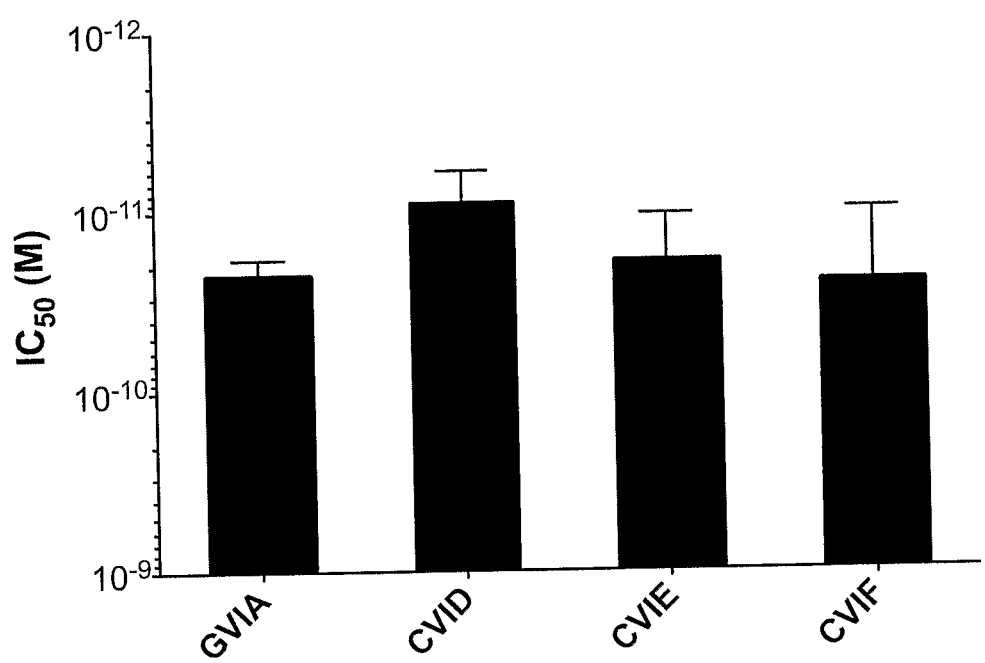
FIG. 1 shows the affinity of ω-conotoxins GVIA, CVID, CVIE and CVIF for rat brain calcium channels, as measured from displacement of $^{125}$I-GVIA binding to rat brain membranes.

Boc-L-amino acids were purchased from Merck (Darmstadt, Germany) and the Peptide Institute (Osaka, Japan). 4-MeBHA resin was from the Peptide Institute. O-(Benzotriazol-1-yl)-N,N,N',N'-tetramethyluronium hexafluorophosphate and reduced and oxidized glutathione were from Sigma-Aldrich Pty Ltd (Sydney, Australia). O-(7-Azabenzotriazol-1-yl)-N,N,N',N'-tetramethyluronium hexafluorophosphate was from Genscript (Piscataway, N.J.). Dichloromethane and NH$_4$OAc were from Merck. N,N-diisopropylethylamine, N,N-dimethylformamide and trifluoroacetic acid (TFA) were from Auspep (Melbourne, Australia). Guanidine HCl was from Amresco (Solon, USA). Other reagents and solvents were analytical reagent grade. ω-conotoxin CVIB was prepared as described previously (Lewis et al., 2000), ω-Agatoxin IVA was purchased from the Peptide Institute. Nifedipine (Sigma) was freshly prepared from a stock solution in ethanol. Various drugs and toxins were diluted to the final concentration immediately before use.

All animal experimentation was performed in accordance with the U.S. National Institutes of Health guidelines and were approved by the University of Queensland and University of Sydney Animal Ethics Committees.

Concentration-response curves were obtained by plotting averaged relative peak current amplitude values (I/I$_0$) vs. toxin concentration and fitting the resulting data by the Hill equation I=I$_0${[CTX]$^n$/(IC$_{50}$$^n$+[CTX]$^n$)}, where I$_0$ is the maximum peak current amplitude, [CTX] the conotoxin concentration, n the Hill coefficient, and IC$_{50}$ the agonist concentration that produces 50% of the maximum response; pIC$_{50}$ values were defined as –log IC$_{50}$. The blocked fraction was determined as I/I$_0$, while the recovered fraction was defined as [(I$_{rec}$–I)/(I$_0$–I)], where I$_0$ is the maximum peak current amplitude, I the blocked current amplitude, and I$_{rec}$ the current amplitude after washout.

The rate of onset of toxin block was obtained by fitting peak current amplitudes recorded during current block by the mono-exponential equation I/I$_0$=A×exp (–t/τ$_{on}$), where A is maximal peak current amplitude, t is time and τ$_{on}$ is the onset time constant. Recovery times were defined as the times required to recover 10, 20, 30, 50, and respectively 70% of the fraction blocked. The offset time constants (τ$_{off}$) were obtained by fitting peak current amplitudes recorded during current recovery from block by a mono-exponential equation I/I$_0$=A[1–exp (–t/τ$_{off}$)], where A is maximal peak current amplitude, t is time, and τ is time constant. The dissociation constant (K$_d$) values were calculated according to K$_d$=K$_{off}$/K$_{on}$ (M), and as previously described, where K$_{off}$=1/τ$_{off}$(s$^{-1}$) and K$_{on}$=(1/τ$_{on}$–K$_{off}$)/[toxin] (M$^{-1}$·s$^{-1}$).

Data are mean±SEM (m, number of experiments). Statistical analyses were performed using the Student's t-test for two groups, and one-way ANOVA or two-way ANOVA for multiple comparisons; differences were considered significant if p<0.05.

Example 1

ω-Conotoxins CVIE and CVIF were identified following a PCR screen of a cDNA library from the piscivorous cone snail *Conus catus*. This PCR approach enables minor conotoxins, which are difficult to isolate from crude venoms, to be identified and sequenced.

*C. catus* venom ducts were emulsified, poly-A$^+$ tailed mRNA extracted using the QuickPrep mRNA purification system (Amersham Pharmacia Biotech, Sydney, Australia), and cDNA libraries produced (Lewis et al., 2000). ω-Conotoxin sequences in the cDNA libraries were then identified using PCR as described previously (Lewis et al., 2000).

PCR of the *C. catus* venom duct cDNA templates resulted in a DNA product of approximately 380-500 bp. Two PCR products that translated to putative mature peptides were named CVIE and CVIF. The amino acid sequence for CVIE is shown in SEQ ID NO: 4. In the following experiments the N-terminus of these peptides is unsubstituted and the C-terminus is a primary amide.

Example 2

CVIE, CVIF, [R10K]CVIE and [R10K]CVIF were manually synthesized using Boc in situ neutralization solid-phase peptide synthesis (Schnolzer et al., 1992).

Peptides were deprotected and cleaved from the resin as described previously (Schnolzer et al., 1992). Syntheses were carried out on 4-MeBHA-resin. For problematic regions O-(7-azabenzotriazol-1-yl)-N,N,N',N'-tetramethyluronium hexafluorophosphate was used as a coupling reagent instead of O-(benzotriazol-1-yl)-N,N,N',N'-tetramethyluronium hexafluorophosphate. Oxidation of the pure reduced peptides (0.05 mM) was achieved using aqueous 0.33 M $NH_4OAc$/0.5 M guanidine HCl (pH 7.8, adjusted with 1 M $NH_4OH$) in the presence of reduced and oxidized glutathione (the molar ratio of peptide:GSH:GSSG was 1:100:10). This solution was stirred at 4° C. for 72 hours to produce the folded peptides. Oxidation was monitored using analytical reversed phase high performance liquid chromatography (RP-HPLC) and mass spectrometry. When oxidation was complete, the pH of the solution was lowered using trifluoroacetic acid (TFA) and the peptides were purified using preparative RP-HPLC.

Peptides were quantified using RP-HPLC with an external reference standard as described previously (Moffatt et al., 2000). Analyses were performed in triplicate using a Shimadzu 2010 Analytical HPLC system (UV measured at 214 nm) with an Agilent Zorbax C18 column (0.21×5 cm, 3.5 µm).

Mass spectra were obtained using an Applied Biosystems API2000 LC/MS/MS triple quadrupole mass spectrometer equipped with an ESI source in positive ion mode (m/z 400-1800, with a declustering potential of 10-20V, and 0.1 Da steps). The molecular weight of the peptide was deduced from the multiply charged species using Analyst v1.4 with Bioanalyst extensions (Applied Biosystems, Carlsbad, Calif.). MALDI-TOF MS data were acquired using an Applied Biosystems 4700 MALDI-TOF-TOF proteomics analyzer in reflector positive mode (m/z 500-5000). α-Cyano-4-hydroxy cinnamic acid (10 mg/ml) was used as the matrix solution.

Analytical reversed phase high performance liquid chromatography (RP-HPLC) was performed on a Shimadzu HPLC system using a Vydac C18 column (0.46×25 cm, 5 µm). Separation was achieved using a linear gradient increasing at 1% solvent B/min with a flow rate of 1 ml/min over 35 mins. Preparative RP-HPLC was performed on a Waters HPLC system using a Vydac C18 column (2.2×25 cm, 10 µm). A linear gradient over 35 min was used, increasing at 1% solvent B/min at a flow rate of 10 ml/min. Solvent A was 0.05% aqueous TFA, solvent B was 90% acetonitrile/$H_2O$ with 0.43% TFA.

Example 3

The affinity of GVIA, CVID, CVIE and CVIF at N-type VGCCs was determined from displacement of $^{125}$I-GVIA binding to rat brain membranes, as described previously (Lewis et al., 2000).

As shown in FIG. 1, synthetic CVIE and CVIF fully displaced $^{125}$I-GVIA binding to rat brain membrane. The affinities of CVIE (37 pM) and CVIF (98 pM) were not significantly different from those of GVIA (24 pM) and CVID (12 pM). The $pIC_{50}$ values for CVIE is 10.7±0.27 M and CVIF is 10.6±0.41 M at VGCCs, whereas the $pIC_{50}$ values for GVIA is 10.6±0.09 M and CVID is 11.0±0.18 M at VGCCs. Data are indicative values, presented as means±SEM from 4-5 separate experiments, each performed in triplicate.

Example 4

Clones of rat $Ca_v2.2$ $α_{1B-b}$ (N-type, peripheral isoform), rat $Ca_v1.3$ $α_{1D}$ (L-type), and rat $β_3$ cDNAs were provided by Dr. D. Lipscombe (Brown University, Providence, R.I.); rabbit $Ca_v1.2$ $α_{1C}$ (L-type), rabbit $Ca_v2.1$ $α_{1A}$ (P/Q-type), rat $Ca_v2.3$ $α_{1E}$ (R-type), and rat $β_{2a}$ cDNAs were provided by Dr. G. Zamponi (University of Calgary, Calgary, Canada). Rabbit $α_2δ1$ cDNA was provided by Dr. F. Hofmann and Dr. N. Klugbauer (Technische Universitat Mtinchen, Germany).

Stage V-VI oocytes from *Xenopus laevis* frogs were surgically removed and cultured as described previously (Yasuda et al., 2004). Capped RNA transcripts encoding full-length VGCC pore-forming and auxiliary subunits were synthesized using the mMessage mMachine in vitro transcription kit (Ambion, Applied Biosystems).

For recombinant N-($Ca_v2.2$) or L-type ($Ca_v1.2$ or $Ca_v1.3$) VGCC expression, the oocytes were injected with 50 nl of solution containing a mixture of cRNAs encoding $α_{1B-b}$ subunit (5 ng/cell) or $α_{1C}$ subunit (5 ng/cell), or $α_{1D}$ subunit (5 ng/cell), and $β_3$ subunit (8 or 12 ng/cell) with or without $α_2δ1$ subunit (5 ng/cell). For $α_{1B-b}$/$α_2δ1$/$β_{2a}$ VGCC expression, 0.5 ng/cell $β_{2a}$ subunit cRNA was used. For recombinant expression of P/Q- or R-type VGCCs, the oocyte nucleus was first injected with 9 nl of cDNA encoding for $Ca_v2.1$ $α_{1A}$ (4.5 ng/cell) or $Ca_v2.3$ $α_{1E}$ (4.5 ng/cell) subunits, respectively, after which the cytoplasm was injected with cRNAs encoding auxiliary subunits.

Following injection, oocytes were kept at 18° C. for 3-7 days for recombinant calcium channel expression, as described previously (Yasuda et al., 2004). Depolarization-activated $Ba^{2+}$ or $Ca^{2+}$ currents ($I_{Ba}$ and $I_{Ca}$, respectively) were recorded using a two-electrode virtual ground voltage-clamp circuit with a GeneClamp 500B amplifier controlled by a Clampex9.2/DigiData1332 acquisition system (Molecular Devices, Sunnyvale, Calif.). Prior to recording, oocytes were injected with 30 nl of 50 mM BAPTA to eliminate endogenous $Ca^{2+}$-activated $Cl^-$ conductance. The oocytes were placed in a 0.1 ml recording chamber and superfused at a constant rate of 3 ml/min. The external bath solution contained (in mM): 5 $BaCl_2$, 85 tetraethylammonium hydroxide (TEA-OH), 5 KCl, 10 HEPES, pH 7.4 (with methanesulfonic acid).

In a series of experiments, 5 mM $BaCl_2$ was substituted by 5 mM $CaCl_2$ in the external bath solution. Borosilicate glass microelectrodes were filled with 3 M KCl and had resistances of 0.4-1.2 MΩ. Oocytes were voltage-clamped at various holding potentials, and membrane currents were elicited by 200 ms step depolarizations to 0 mV ($Ca_v2.2$ and $Ca_v1.2$), +10 mV ($Ca_v2.1$), +10 mV ($Ca_v2,3$), or −30 mV ($Ca_v1.3$), applied every 10 s. Experiments were only commenced when the alteration of peak current evoked by repeated depolarizing pulses was reduced to less than ±2% within a 1 min period (Yasuda et al., 2004). Leak and capacitive currents were subtracted using a −P/4 pulse protocol and current amplitudes were monitored on-line using the Clampex 9.2 software package. Currents were filtered at 1 or 2 kHz, digitized at 5 kHz and stored on a computer hard-drive.

ω-Conotoxins CVIE and CVIF (0.1-3 µM) potently inhibited depolarization-activated $Ba^{2+}$ currents ($I_{Ba}$) through $Ca_v2.2$ channels expressed in *Xenopus* oocytes. The oocytes were injected with $Ca_v2.2$ VGCC $α_{1B-b}$, $α_2δ1$, and $β_3$ cRNAs.

Figure 2:
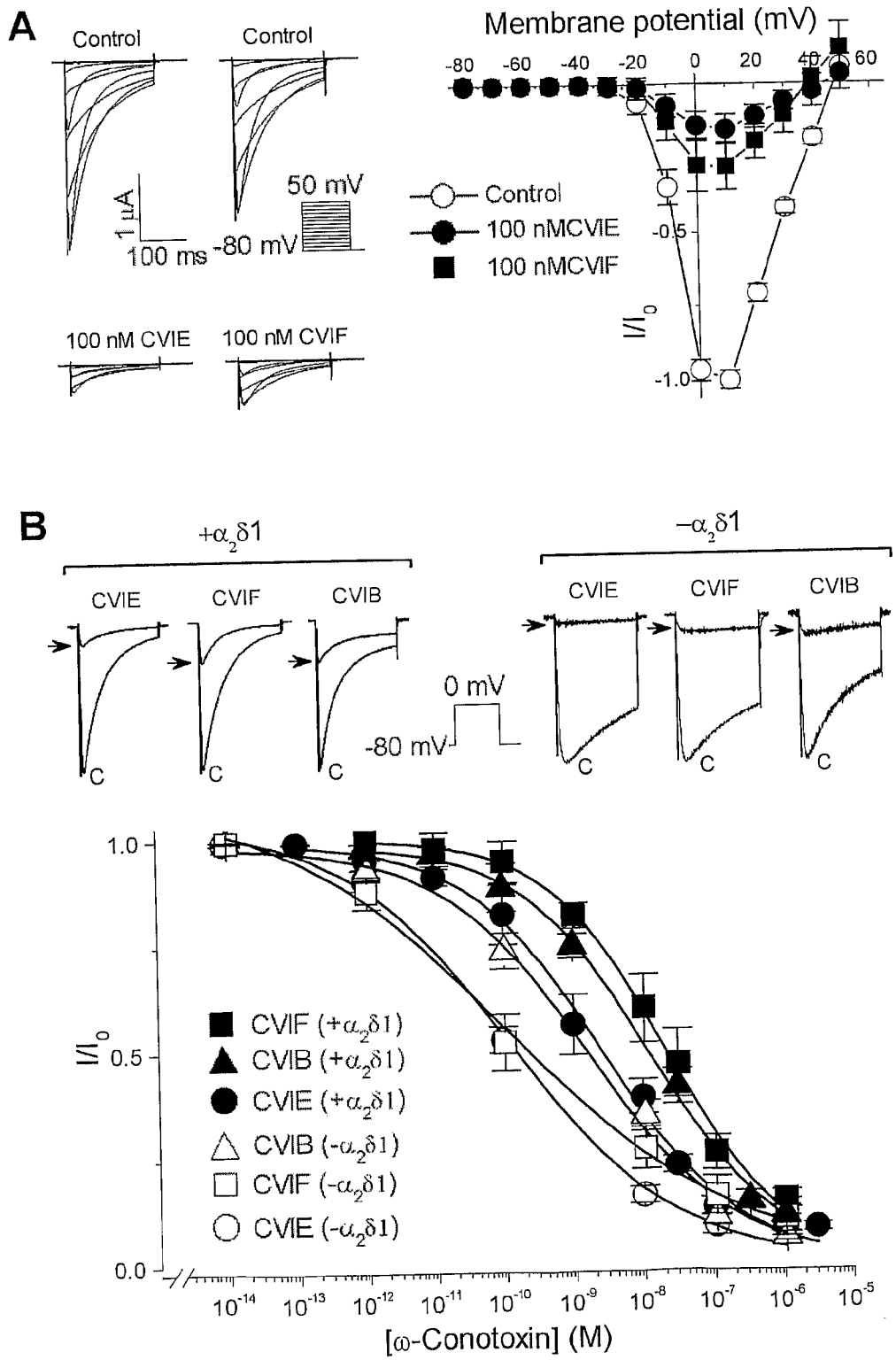
FIG. 2 shows inhibition of recombinant N-type (Ca$_v$2.2) VGCCs expressed in *Xenopus* oocytes by ω-conotoxins in the presence or absence of expressed α$_2$δ$_1$ subunit.

As shown in FIG. 2A, $I_{Ba}$ was measured in the absence of CVIE and CVIF as a control. Measurements were also obtained in the presence of 100 nM CVIE (n=4) and 100 nM CVIF (n=5). The corresponding normalized current-voltage relationships are shown at the right of FIG. 2A. Currents were evoked by 200 ms depolarizing voltage steps in 10 mV increments at every 10 s, from a holding potential (HP) of −80 mV, as shown in the inset voltage protocol.

At the highest concentration tested (3 μM), neither peptide had any effect on recombinant $Ca_v1.2$, $Ca_v1.3$, or $Ca_v2.3$ channels (n≥5 in all cases) assembled from pore-forming α and auxiliary $α_2δ1$ and $β_3$ subunits. However, 3 μM CVIE or CVIF caused a minor (<10%) inhibition of $Ca_v2.1$ (α, $α_2δ1$, $β_3$) channels (n≥5).

$I_{Ba}$ was recorded in the absence and presence of a single concentration (100 nM) of ω-conotoxin CVIE, CVIF or CVIB for comparison, as shown in FIG. 2B. FIG. 2B shows representative normalized $I_{Ba}$ traces obtained before (C, control) and after (arrowhead) application of 100 nM ω-conotoxin CVIE, CVIF, or CVIB from oocytes injected with $α_{1B-b}/α_2δ1/β_3$ or $α_{1B-b}/β_3$ $Ca_v2.2$ VGCC cRNAs. Currents were evoked by 200 ms step depolarizations to 0 mV from a HP of −80 mV, as shown in the inset voltage protocol.

Cumulative concentration-response curves for the normalized peak $I_{Ba}$ in the presence or absence of the auxiliary $α_2δ_1$ $Ca^{2+}$ channel subunit are displayed at the bottom of FIG. 2B. Increasing concentrations of ω-conotoxin were applied to produce cumulative concentration-response relationships. In each case, the solid curve is the best fit. These relations were described by Hill equations with $IC_{50}$ and Hill slope values of 2.6±0.5 nM and 0.45±0.03 (n=14) for CVIE, 19.9±3.2 nM and 0.51±0.04 (n=16) for CVIF, and 12.0±2.3 nM and 0.47±0.03 (n=8) for CVIB, respectively. In the absence of $α_2δ1$, the following $IC_{50}$ and Hill slope values were obtained: 0.12±0.05 nM and 0.36±0.04 (n=6) for CVIE, 0.1±0.07 nM and 0.26±0.04 (n=7) for CVIF, and 1.6±0.6 nM and 0.41±0.04 (n=5) for CVIB, respectively. N-type $Ca^{2+}$ channel inhibition by any of the above ω-conotoxins was ~10-20 fold more potent in the absence of the $α_2δ_1$ auxiliary subunit compared to that observed in the presence of $α_2δ_1$.

It was also found that in the concentration range between 0.1 and 1 μM, neither [R10K]CVIE or [R10K]CVIF had any effect on $Ca_v1.2$ (n=4 and n=3, respectively), $Ca_v1.3$ (n=3 and n=3, respectively), $Ca_v2.1$ (n=6 and n=6, respectively), or $Ca_v2.3$ (n=3 and n=3, respectively) recombinant ($α/α_2δ_1/β_3$) channels. Both compounds blocked $α_{1B-b}/α_2δ_1/β_3$ or $α_{1B-b}/α_2δ_1/β_{2a}$ VGCCs in a dose dependent manner, as shown in FIG. 3A.

Figure 3:
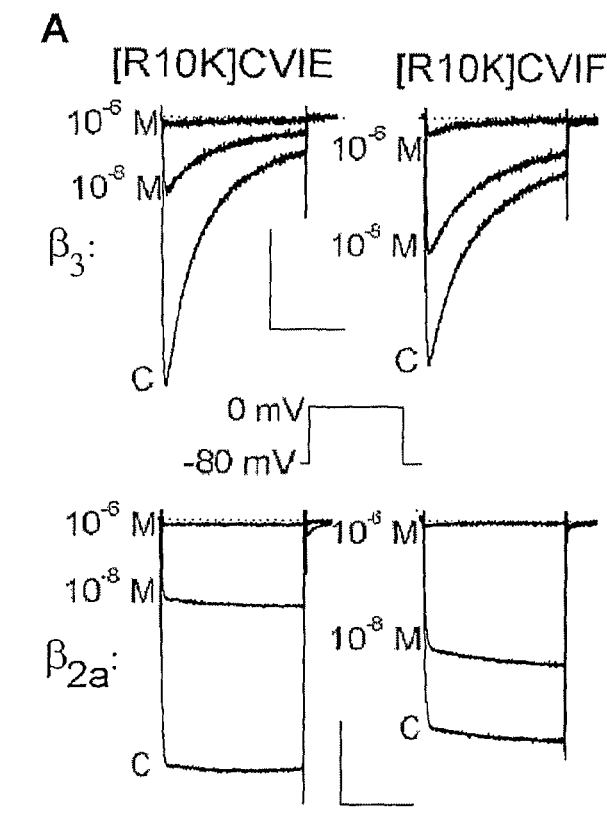
FIG. 3 shows that [R10K]CVIE and [R10K]CVIF block recombinant N-type (Ca$_v$2.2) VGCCs in *Xenopus* oocytes.
Figure 3:
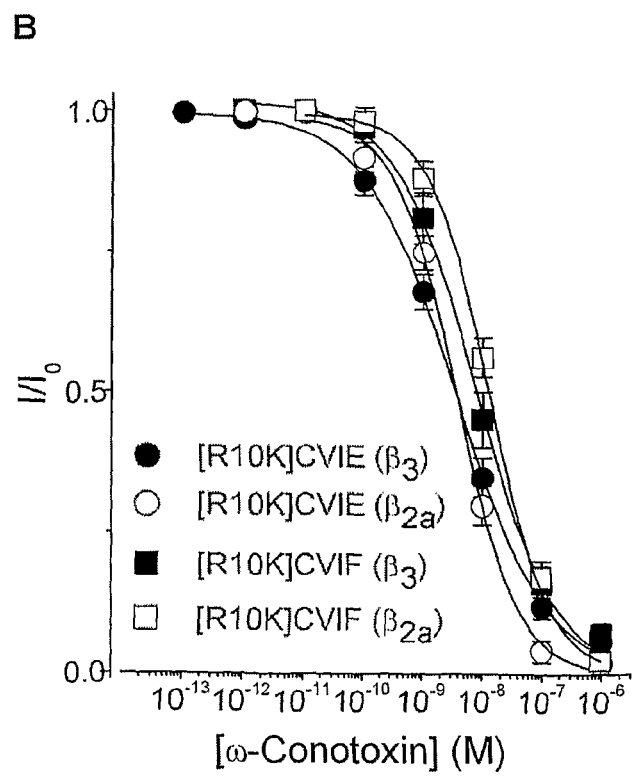

FIG. 3A shows representative superimposed traces of $I_{Ba}$ obtained in the absence (C, control) and presence of increasing concentrations ($10^{-8}$ and $10^{-6}$ M) of [R10K]CVIE or [R10K]CVIF, from oocytes expressing fast-inactivating N-type ($α_{1B-b}/α_2δ1/β_3$) (top) or slowly-inactivating N-type ($α_{1B-b}/α_2δ1/β_{2a}$) (bottom) VGCCs. $I_{Ba}$ were evoked by 200-ms depolarizing voltage steps applied at every 10 s (protocol inset). The dotted lines indicate zero-current level; the vertical bars represent 0.5 (top) or 1 μA (bottom); and the horizontal bars represent 100 ms.

The dose dependence of the block was described by Hill equations resulting in $IC_{50}$ and Hill slope values of 3.5±0.3 nM and 0.57±0.02 ($α_{1B-b}/α_2δ1/β_3$); 3.6±0.3 nM and 0.84±0.05 ($α_{1B-b}/α_2δ1/β_{2a}$) for [R10K]CVIE, and of 7.6±0.9 nM and 0.65±0.04 ($α_{1B-b}/α_2δ1/β_3$); 12.8±0.8 nM and 0.86±0.04 ($α_{1B-b}/α_2δ1/β_{2a}$) for [R10K]CVIF, respectively, as shown in FIG. 3B. FIG. 3B shows cumulative concentration-response curves for [R10K]CVIE or [R10K]CVIF inhibition of N-type VGCCs with a fast ($α_{1B-b}/α_2δ1/β_3$) or profoundly slow ($α_{1B-b}/α_2δ1/β_{2a}$) time course of inactivation. For each data point n≥5, solid curves represent the best fit with the Hill equation. These $IC_{50}$ values are similar to those reported for CVIE and CVIF, indicating that the R10K chemical modification did not alter selectivity or potency of CVIE or CVIF for recombinant N-type VGCCs.

Figure 4:
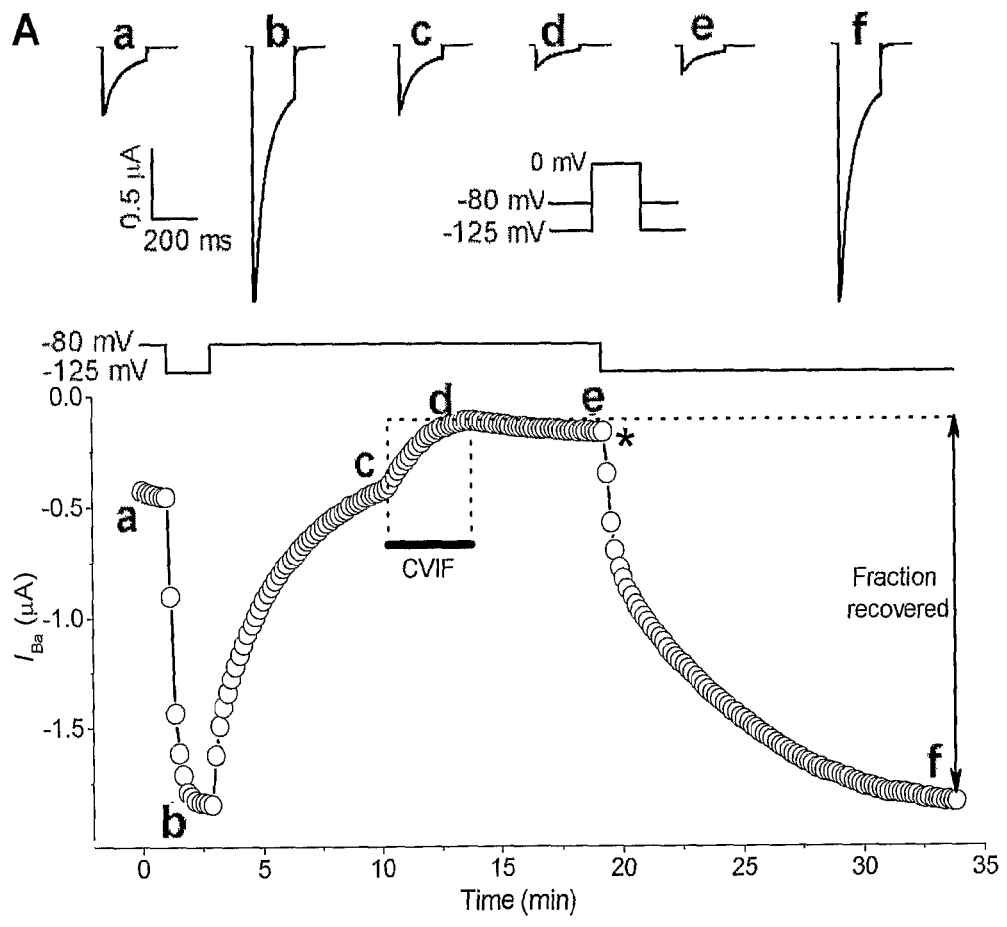
FIG. 4 illustrates that at recombinant N-type (Ca$_v$2.2) VGCCs expressed in oocytes, recovery from block by CVIE and CVIF is voltage dependent.
Figure 4:
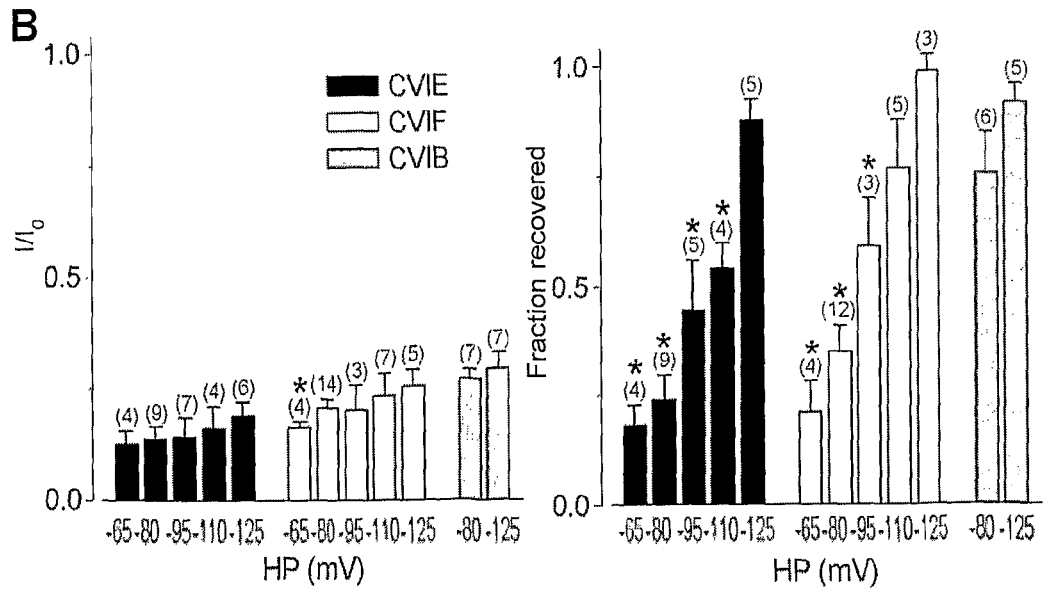

As shown in FIG. 4A, the holding potential (HP) affects peak $I_{Ba}$ amplitude and recovery from block by ω-conotoxin CVIF. $I_{Ba}$ was evoked by 200 ms, 0.1 Hz depolarizations to 0 mV from holding potentials of −80 or −125 mV. Recombinant ($α_{1B-b}$, $α_2δ_1$, $β_3$) N-type VGCC availability from HPs of −80 or −125 mV was first assessed in the absence of ω-conotoxin. Robust inactivation of N-type channels was exhibited at a HP of −80 mV. However, channels rapidly became available when the HP was changed from −80 mV to −125 mV (as shown by the voltage insets), and inactivated following a simple exponential time course (which could be best described by the sum of two exponential functions) when the membrane potential was returned to −80 mV. Representative current traces are shown at the top of FIG. 4A at the times indicated by the lower case letters.

At −80 mV, when the peak $I_{Ba}$ reached quasi steady-state amplitude, 100 nM CVIF or CVIE (n=2) was applied until complete block developed, after which the toxin was washed off. Recovery from ω-conotoxin block was strongly affected by the HP. As shown by the asterisk in FIG. 4A, at −80 mV recovery was slow and incomplete, but upon return to −125 mV the current fully recovered to its pre-toxin, hyperpolarized −125 mV HP level.

As the duration of these experiments often exceeded 40-50 min, run-down of the $I_{3a}$ could occur and, despite BAPTA injection, endogenous (background) currents could develop. To limit these currents, $I_{Ba}$ from oocytes with relatively low $Ca^{2+}$ channel expression levels (just 36-48 h after injection) was recorded, and the inactivation-recovery time (from a to b; FIG. 4A) and inactivation time (from b to c; FIG. 4A) were limited. Consequently, full recovery or full inactivation, respectively, was only approached. This, however, did not significantly affect the outcome of the experiment.

As shown in FIG. 4B, the fractions of currents blocked and recovered were examined in the voltage range between −65 and −125 mV following bath application and washout of 100 nM ω-conotoxin CVIE, CVIF or CVIB. Oocytes were voltage-clamped at the indicated holding potentials, and membrane currents were elicited by 200 ms step depolarizations to 0 mV, applied every 10 s. Asterisks denote statistical differences between −125 mV and various HPs (*p<0.05, one-way ANOVA), and the numbers between parentheses indicate the number of experiments.

Recovery of recombinant N-type VGCCs from CVIE and CVIF block exhibited voltage dependence, whereas recovery of recombinant N-type VGCCs from CVIB block does not. For CVIE and CVIF, the HP generally had statistically non-significant effects on the fraction blocked (as shown on the left of FIG. 4B); however the HP strongly determined the fraction of current recovery from block (as shown on the right of FIG. 4B). For example, at −65 mV HP, the current recovered only partially from CVIF block (20.3±3.9%, n=4), whereas at −125 mV the recovery was almost complete (99±4%, n=3). Similarly, in the absence of the $α_2δ_1$ subunit, the recovery from CVIE or CVIF block was voltage dependent, which persisted upon replacement of $Ba^{2+}$ as the charge carrier with the physiological ion, $Ca^{2+}$. This data suggests that CVIE and CVIF have higher affinity for the inactivated state of the N-type $Ca^{2+}$ channels.

The kinetics of ω-conotoxin action was affected by the R10K substitution, resulting in faster onset and recovery of block compared to CVIE or CVIF. For example, with $\alpha_{1B-b}/\alpha_2\delta 1/\beta_3$ channels, and holding potentials of −80 or −125 mV, the time constants of block ($\tau_{on}$) with [R10K]CVIE were 15.2±0.8 (s) and 22.8±0.8 (s), respectively. This was about two times faster than those for CVIE, which were 31.5±2.4 (s) and 38.5±2.8 (s), respectively, as shown in FIG. 5A.

Figure 5:
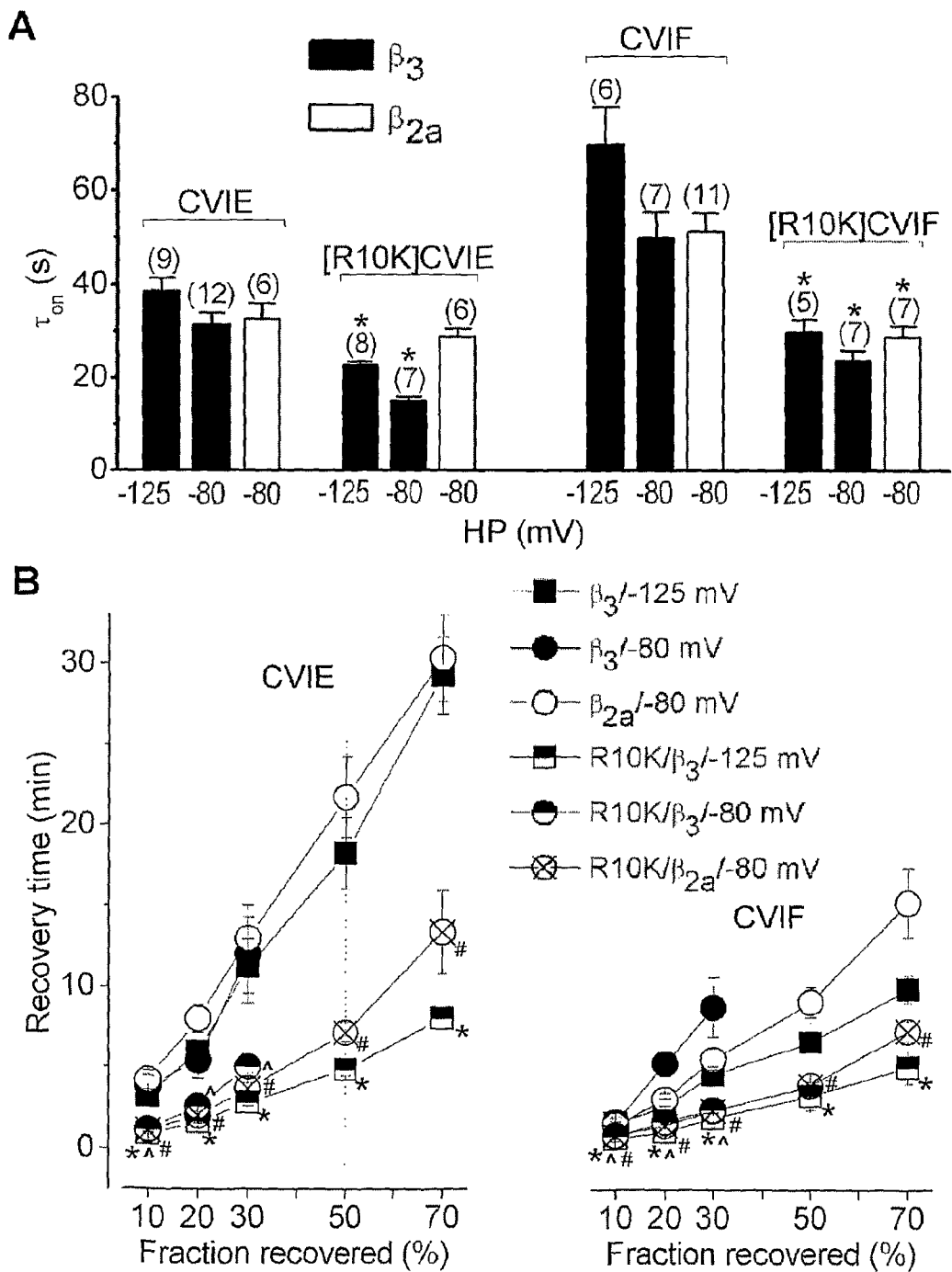
FIG. 5 shows that the R10K substitution affects the kinetics of ω-conotoxin block and recovery in oocytes expressing N-type (α$_{1B-b}$/α$_2$δ1/β$_3$) or (α$_{1B-b}$/α$_2$δ1/β$_{2a}$) VGCCs.

FIG. 5A shows the time constants of block by CVIE, CVIF, and their R10K analogs. The numbers between parentheses indicates the number of experiments, and asterisks denote statistical differences resulting from pairwise comparison of [R10K]CVIE and CVIE or [R10K]CVIF and CVIF (at identical conditions) (*p<0.001, unpaired Student's t-test). As can be seen in FIG. 5A, the time constants exhibit voltage dependence with $\alpha_{1B-b}/\alpha_2\delta 1/\beta_3$ VGCCs.

As shown in FIG. 5B, the times required to effect 10, 20, 30, 50, and 70% recovery during washout of [R10K]CVIE or [R10K]CVIF were 2-5 times faster compared to CVIE or CVIF, respectively. For each data point in FIG. 5B, n≥5 and * indicates statistical differences (p<0.05) between [R10K] CVIE/$\beta_3$/−125 mV or [R10K]CVIF/$\beta_3$/−125 mV and CVIE/$\beta_3$/−125 mV or CVIF/$\beta_3$/−125 mV, respectively (one-way ANOVA). ^ indicates statistical differences (p<0.05) between [R10K]CVIE/$\beta_3$/−80 mV or [R10K]CVIF/$\beta_3$/−80 mV and CVIE/$\beta_3$/−80 mV or CVIF/$\beta_3$/−80 mV, respectively (one-way ANOVA). # indicates statistical differences (p<0.05) between [R10K]CVIE/$\beta_{2a}$/−80 mV or [R10K]CVIF/$\beta_{2a}$/−80 mV and CVIE/$\beta_{2a}$/−80 mV or CVIF/$\beta_{2a}$/−80 mV, respectively (one-way ANOVA).

The link between N-type VGCC inactivation and the reversibility of ω-conotoxin action was investigated further by creating molecular diversity in the β subunits, resulting in VGCCs with a fast ($\alpha_{1B-b}/\alpha_2\delta 1/\beta_3$) or profoundly slow ($\alpha_{1B-b}/\alpha_2\delta 1/\beta_{2a}$) time course of inactivation.

Figure 6:
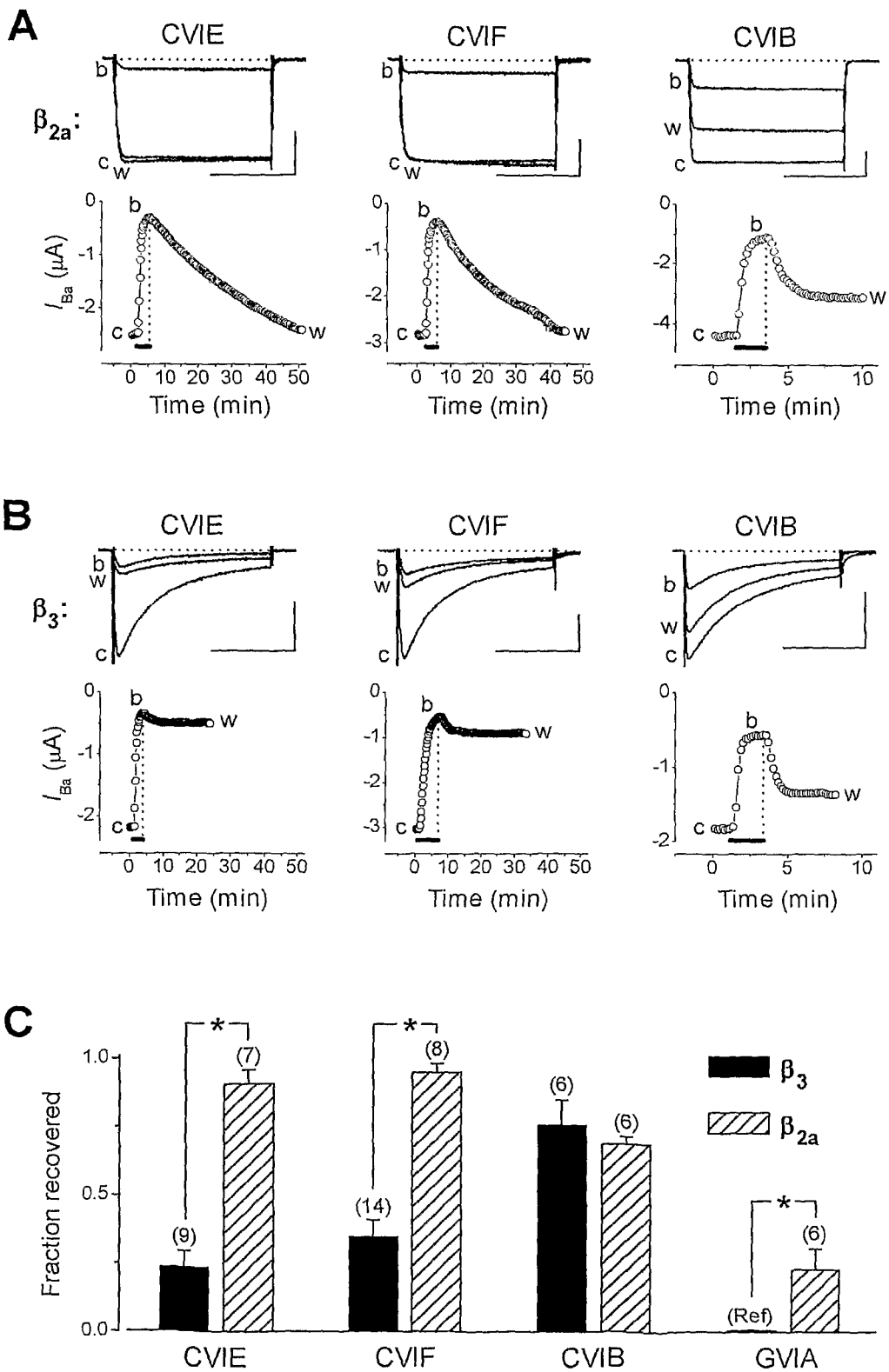
FIG. 6 shows that in *Xenopus* oocytes, the recovery of non-inactivating N-type (α$_{1B-b}$/α$_2$δ1/β$_{2a}$) VGCCs from CVIE or CVIF block is reversible.
Figure 7:
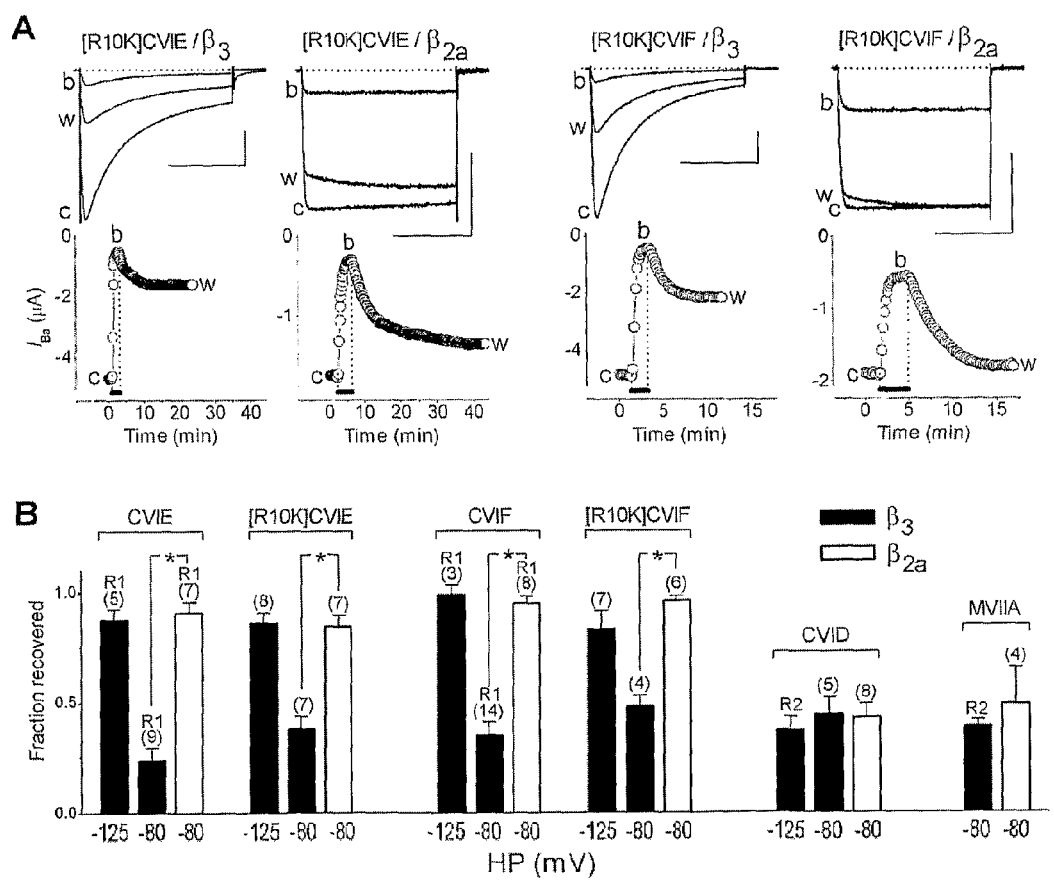
FIG. 7 illustrates the recovery of VGCCs from ω-conotoxin block in the presence of β$_3$ or β$_{2a}$ subunits.
Figure 8:
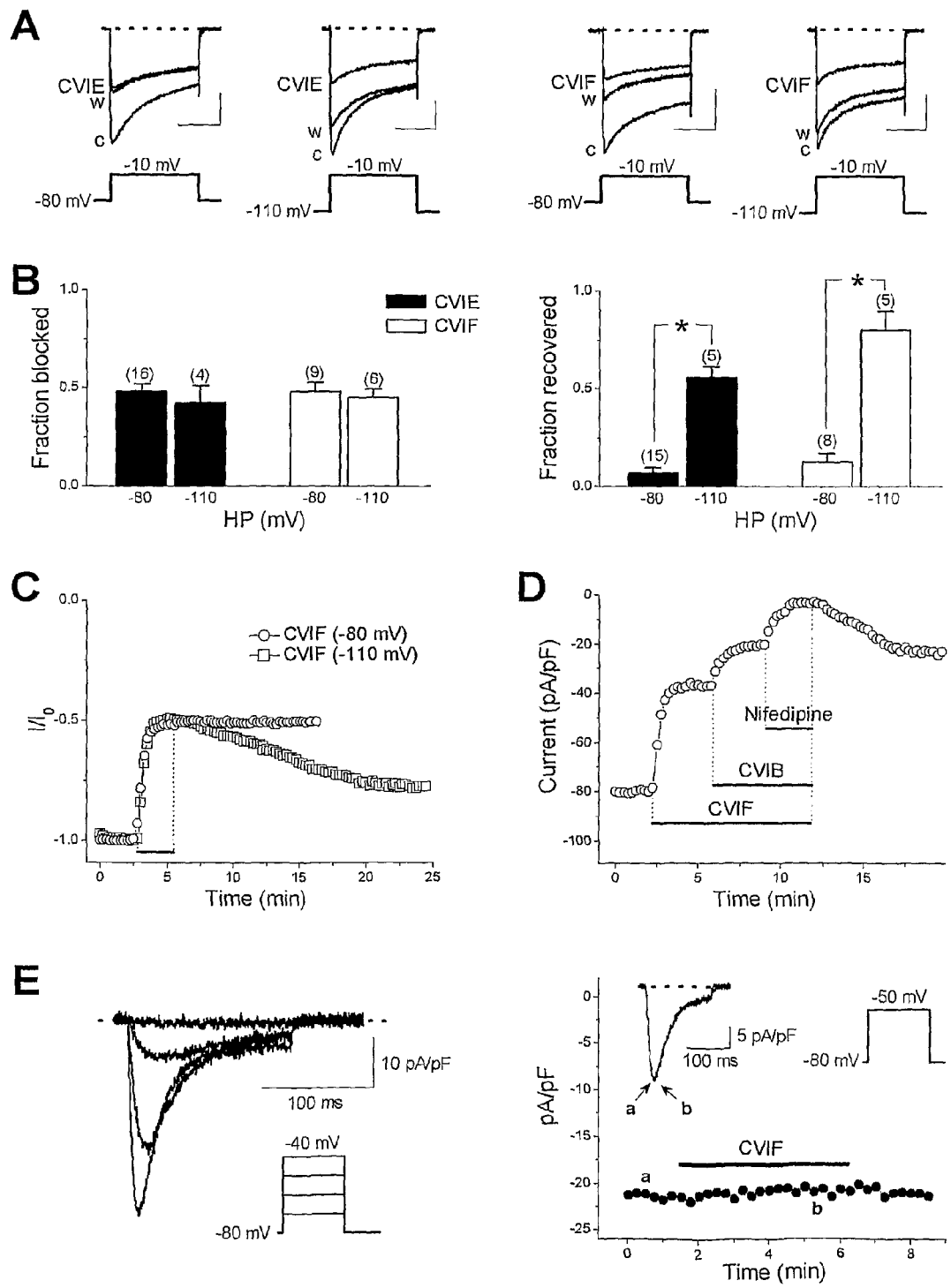
FIG. 8 shows VGCC inhibition by ω-conotoxins CVIE and CVIF and voltage-dependent recovery from block in acutely dissociated rat dorsal root ganglion (DRG) neurons.

The $I_{Ba}$ at $\alpha_{1B-b}/\alpha_2\delta 1/\beta_{2a}$ VGCCs (FIG. 6A) and $\alpha_{1B-b}/\alpha_2\delta 1/\beta_3$ VGCCs (FIG. 6B) was measured in the absence (c, control; w, wash) and presence of 100 nM CVIE, CVIF, or CVIB (b, block), evoked by 200-ms depolarizing pulses to 0 mV from a HP of −80 mV, at 0.1 Hz. In the upper figures of each of FIGS. 6A and 6B, the bars are 1 μA and 100 ms and dashed lines indicate zero-current level, and in the lower figures peak current amplitudes were plotted as a function of time, with the horizontal bars indicating the duration of drug application.

The reversibility of block following bath application of 100 nM ω-conotoxin CVIE, CVIF, CVIB, or GVIA, seen with $\alpha_{1B-b}/\alpha_2\delta 1/\beta_{2a}$, or $\alpha_{1B-b}/\alpha_2\delta 1/\beta_3$ VGCCs, is illustrated in FIG. 6C. In this Figure, the numbers between parentheses indicate the number of experiments, asterisks denote statistical differences (*p<0.001, unpaired Student's t-test), and data marked by "Ref" is from Mould et al. (2004) and represents recovery from block by 1 nM GVIA.

At a HP of −80 mV, VGCCs with $\beta_{2a}$ subunits almost recovered completely from CVIE or CVIF block (FIGS. 6A and 6C), whereas VGCCs with $\beta_3$ subunits exhibited relatively weak recovery (FIGS. 4B, 6B-C). The HP did not affect recovery of N-type channels with $\beta_{2a}$ subunits from CVIE or CVIF block, as full recovery was also obtained at −125 mV (n=3).

ω-Conotoxins closely related to CVIE and CVIF were also tested including GVIA, which was previously shown to have weak voltage-dependent reversibility compared to CVIE or CVIF, and CVIB, which was shown to lack voltage-dependent reversibility. Recovery from GVIA block also appeared to be β subunit-dependent (FIG. 6C). However, the $I_{Ba}$ fraction recovered from CVIB block was not affected by auxiliary β subunits (FIGS. 4B, 6A-C).

The recoverable component of N-type channel currents was determined after block by the R10K analogs or various ω-conotoxins, as shown in FIG. 7. VGCCs with profoundly slow inactivation ($\alpha_{1B-b}/\alpha_2\delta 1/\beta_{2a}$) exhibited efficient recovery, whereas the recovery of VGCCs with fast inactivation ($\alpha_{1B-b}/\alpha_2\delta 1/\beta_3$) was weaker, as shown in FIG. 7A. At the top of FIG. 7A representative superimposed traces are provided of $I_{Ba}$ evoked by 200-ms, 0.1-Hz depolarizing pulses to 0 mV from a holding potential of −80 mV, in the absence (c, control; w, wash) and presence of $10^{-7}$ M [R10K]CVIE or [R10K] CVIF (b, block). The bars represent 1 μA and 100 ms and the dotted lines indicate zero-current level. The bottom of FIG. 7A shows peak current amplitudes plotted as a function of time. The horizontal bars indicate the duration of drug application.

As shown in FIG. 7B, $\alpha_{1B-b}/\alpha_2\delta 1/\beta_3$ channel recovery from block by R10K analogs was strongly determined by the holding potential (HP), whereas recovery of VGCCs with $\beta_{2a}$ subunits was independent of the holding potential. Previous experiments demonstrated that recovery of $\alpha_{1B-b}/\alpha_2\delta 1/\beta_3$ channels from CVID block was not affected by HP (Mould et al. 2004), whereas recovery from MVIIA block exhibited a relatively weak voltage dependency (Stocker et al. 1997). Recovery of recombinant N-type VGCCs from block by CVID or MVIIA could not be improved by replacing $\beta_3$ subunits with $\beta_{2a}$, as shown in FIG. 7B.

FIG. 7B shows the reversibility of block by $10^{-7}$ M ω-conotoxin CVIE, [R10K]CVIE, CVIF, [R10K]CVIF, CVID, or MVIIA, seen with $\alpha_{1B-b}/\alpha_2\delta 1/\beta_{2a}$, or $\alpha_{1B-b}/\alpha_2\delta 1/\beta_3$ VGCCs. In all cases, a similar experimental protocol was employed as in FIG. 7A. The numbers between parentheses indicate the number of experiments and asterisks denote statistical differences (*p<0.001, unpaired Student's t-test). Data marked by R1 and R2 is from FIG. 6 and Mould et al. (2004), respectively. As illustrated in FIG. 7B, a holding potential of −125 mV also alleviates $\alpha_{1B-b}/\alpha_2\delta 1/\beta_3$ VGCC recovery from block by CVIE, CVIF, or by their R10K analogs.

Example 5

DRG neurons were enzymatically dissociated from ganglia of 6-14 day-old Wistar rats, as described previously (Motin et al., 2007) and used for experiments within 24-48 h. Cells were transferred into a small-volume (~200 μl) recording chamber constantly perfused with a solution containing (in mM): 150 tetraethylammonium chloride (TEA-Cl), 2 $BaCl_2$, 10 D-glucose, 10 HEPES, pH 7.4 (with NaOH). Borosilicate glass electrodes were filled with an internal solution containing (in mM): 140 CsCl, 1 $MgCl_2$, 5 MgATP, 0.1 Na-GTP, 5 BAPTA-$Cs_4$, 10 HEPES, pH 7.3 (with CsOH) and had resistances of 1.5-2.5 MΩ. Patch-clamp recordings were performed with Multiclamp 700B amplifiers controlled by Clampex9.2/DigiData1332 acquisition systems (Molecular Devices), at room temperature (23-25° C.). Unless indicated otherwise, whole-cell $I_{Ba}$ was elicited by 200 ms step depolarizations to 0 mV, applied every 15 s, from a holding potential of −80 mV, in the voltage-clamp configuration of the patch-clamp technique. Currents were filtered at 2 kHz and sampled at 5 kHz. Leak and capacitative currents were subtracted using a −P/4 pulse protocol. Data were stored digitally on a computer for further analysis.

To assess any differences in pharmacology at native versus cloned VGCCs, the selectivity and reversibility of CVIE and CVIF was evaluated at native N-type VGCCs in acutely dissociated DRG sensory neurons (FIG. 8). Representative superimposed traces of $I_{Ba}$ are shown in FIG. 8A, obtained in the absence (c, control; w, wash) and presence of 100 nM CVIE or CVIF. In FIG. 8A, dashed lines indicate zero-current level, the bars are 1 nA and 100 ms, and the voltage protocols are displayed inset. Membrane currents were elicited by 200 ms step depolarizations, applied every 10 s. FIG. 8B shows normalized fractions of blocked (left) and recovered (right) $I_{Ba}$ versus the HP. In this figure, the numbers in parentheses represent the number of cells and asterisks denote statistical differences (*p<0.05, unpaired Student's t-test). FIG. 8C shows a representative time course of onset and recovery from block of $I_{Ba}$ amplitude by CVIF at HPs of −80 and −110 mV. The horizontal bar indicates the duration of drug application.

Both CVIE and CVIF (100 nM) inhibited whole-cell $Ba^{2+}$ currents through VGCCs, and the recovery from block was voltage dependent (FIGS. 8A-C). The maximum inhibition of inward $Ba^{2+}$ current produced by 100 nM CVIE or CVIF in DRG neurons was ~50% (FIG. 8B), which is similar to that reported previously for N-type selective ω-conotoxins CVID, MVIIA, or GVIA (Motin et al., 2007). The residual $I_{Ba}$ in the presence of these ω-conotoxins (1 µM) represents non-N-type current through other (mostly L-, P/Q-, and R-type) VGCCs, which can be selectively blocked (Motin et al., 2007).

As shown in FIG. 8D, the inhibition of peak $I_{Ba}$ by 10 µM nifedipine in the presence of 500 nM CVIB and 1 µM CVIF (n=2) was measured over time. Horizontal bars indicate the sequence and duration of drug application and membrane currents were elicited by 200 ms step depolarizations to −10 mV, applied every 15 s, from a holding potential of −80 mV. CVIB and nifedipine were used to inhibit P/Q- and L-type VGCC currents, respectively. This demonstrates that CVIF does not affect P/Q- and L-type VGCC current components. Similar results were obtained with CVIE (n=4). In two cases, 100 nM of co-agatoxin-IVA was used instead of CVIB, producing the same effect.

In 21% of cells studied (15/70), a low-voltage-activated T-type VGCC was identified using depolarizing voltage steps negative to −40 mV (i.e. weak depolarizations above HP). As shown on the left of FIG. 8E, representative superimposed T-type $Ba^{2+}$ currents in a DRG neuron (21 pF) were elicited by 150 ms step depolarizations in 10 mV increments, applied every 5 s, from a HP of −80 mV. The voltage protocol is shown inset and currents were elicited by 150 ms step depolarizations, applied every 15 s.

T-type current peak amplitude was tested over time in a DRG neuron (41 pF) in the absence and presence of 1 µM CVIF. As shown on the right of FIG. 8E, at the highest concentration tested (1 µM), these channels were not affected by CVIF (n=3). In this Figure, the dashed lines indicate zero-current level and representative traces are shown at the times indicated by lower case letters (the voltage protocol is inset). Similar results were obtained with CVIE (n=3).

Example 6

The spinal cord was isolated from 8-15 day-old Wistar rats as previously described (Motin and Adams, 2008). Before experiments, slices were kept in artificial cerebrospinal fluid for 1 h at 37° C. In spinal cord slices, lamina I-II neurons of the rat superficial dorsal horn were located using an infrared camera. Patch-clamp borosilicate glass electrodes (Harvard Apparatus Ltd., Edenbridge, UK) were filled with a solution containing (in mM): 130 KF, 10 KCl, 10 EGTA, 1 $MgCl_2$, and 10 HEPES (pH 7.2 with KOH), resulting in resistances of 1.5-3 MΩ. The calculated liquid junction potential of 6.4 mV was not compensated. Upon formation of whole-cell recording configuration, neurons were first held in current-clamp configuration to evaluate their resting membrane potential and responses to depolarizing current injections. Excitatory postsynaptic currents (EPSCs) were recorded under voltage-clamp conditions, from a holding potential of −80 mV, in the presence of 100 µM picrotoxin and 10 µM strychnine to block inhibitory synaptic transmission, and were categorized as monosynaptic or polysynaptic responses, as described previously (Motin and Adams, 2008). EPSC amplitude was monitored on-line using Clampex 9.2 software package. Data were filtered at 10 kHz, digitized at 50 kHz and stored on a computer for further analysis. Off-line analysis was performed using custom-written software in MATLAB (The Mathworks Inc., Natick, Mass.), as described previously (Motin and Adams, 2008).

Multiple types of presynaptic VGCCs contribute to neurotransmitter release at peripheral and central synapses. The experimental model mimics the propagation of a nociceptive signal along primary afferents following the electrical stimulation of the dorsal root. Recordings were made from neurons confined within the substantia gelatinosa—the region where Aδ- and C-fibers terminate. The effects of the ω-conotoxins CVIE (100 nM) and CVIF (100 nM) were examined on the excitatory synaptic transmission between primary afferents and dorsal horn superficial lamina neurons, a process predominantly, if not entirely, controlled by N-type VGCCs.

Figure 9:
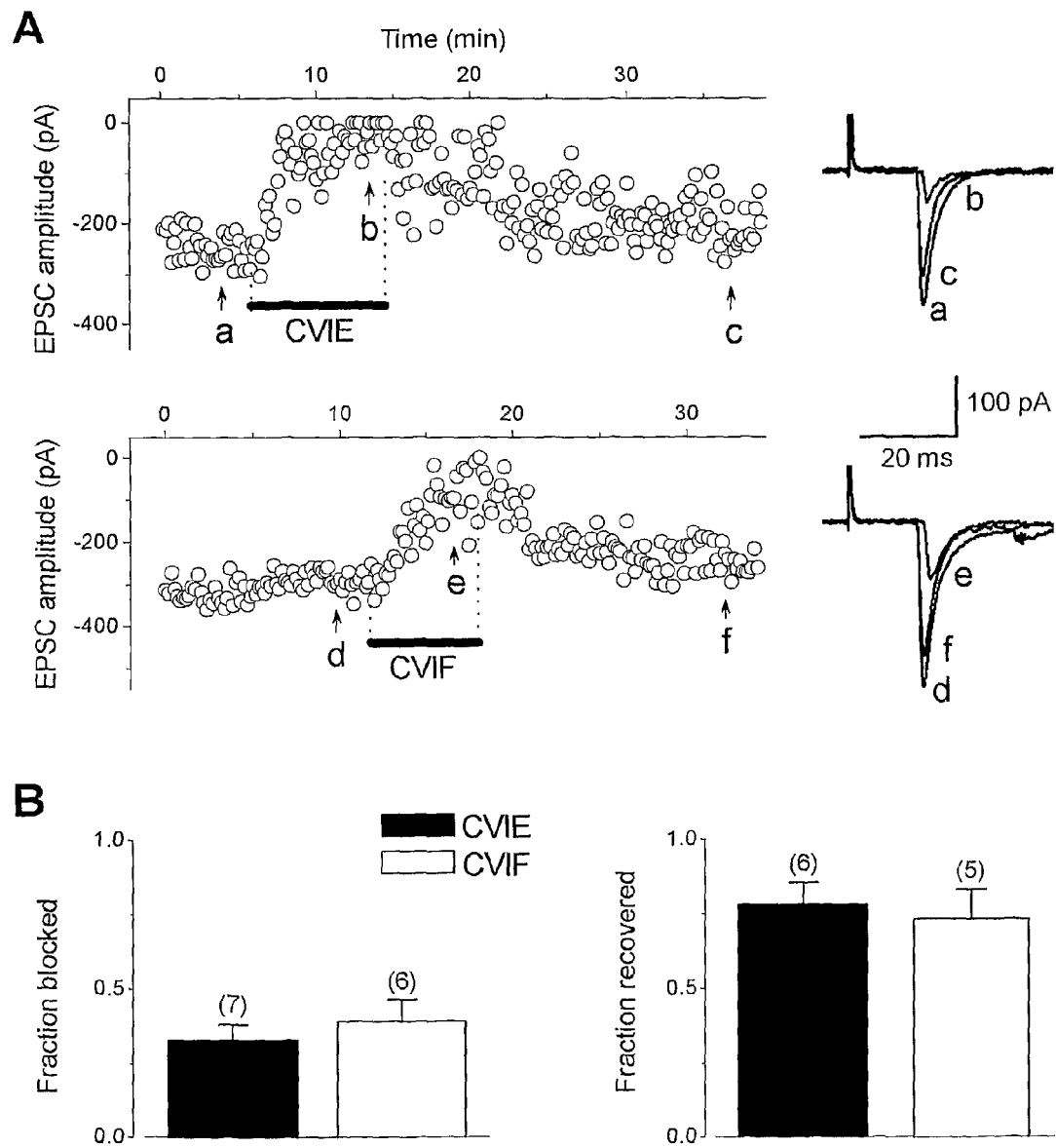
FIG. 9 shows the effect of ω-conotoxins CVIE and CVIF on evoked excitatory postsynaptic currents (EPSCs) in superficial dorsal horn neurons receiving polysynaptic input.

As shown in FIG. 9, inhibition of excitatory synaptic transmission by CVIE and CVIF was reversible. FIG. 9A shows a time course of the inhibition of EPSC amplitude by 100 nM CVIE (top) and 100 nM CVIF (bottom). EPSCs were elicited by electrically stimulating the dorsal root with 0.1 ms pulses applied every 10 s via a bipolar electrode at room temperature (23-25° C.) and peak EPSC amplitude was plotted as a function of time. Data were filtered at 10 kHz, and digitized at 50 kHz. A representative superimposed average of 5 EPSCs is displayed inset to the time course of the inhibition, recorded at the times indicated by arrowheads.

Application of 100 nM CVIE and CVIF reversibly reduced evoked monosynaptic EPSC amplitude by an average of 67±5% (n=7) and 61±7% (n=6), respectively, compared to control, as shown on the left of FIG. 9B. Following washout, the EPSC amplitude recovered to 78±7% and 73±10% of control 10-15 min after block by CVIE (n=6) and CVIF (n=5), respectively, as shown on the right of FIG. 9B. In these experiments, the HP was −80 mV.

Example 7

Experiments were performed on 24 male Sprague-Dawley rats weighing 200-260 g. Rats were housed four per cage and were maintained on a standard 12-h light/dark cycle with free access to food and water. Rats underwent partial ligation of the left sciatic nerve (PNL) (Seltzer et al., 1990), as previously described (Ekberg et al., 2006). In rats that developed significant mechanical allodynia 7 days after surgery, chronic polyethylene lumbar intrathecal catheters were inserted between vertebrae L5 and L6, advanced 3 cm rostrally and exteriorized via the occipital region. All of these procedures were carried out under isoflurane anesthesia. Intrathecal injections were made via the exteriorized catheter 10-12 days after partial nerve ligation (PNL) surgery using gentle restraint. Peptides were dissolved in 0.9% saline to the desired concentration on the day of the experiment and were injected in a volume of 10 µl, followed by 15 µl of 0.9% saline to wash the drug from the catheter dead-space. Control animals received injections of the corresponding vehicle. Mechanical paw withdrawal threshold (PWT) was measured with a series of von Frey hairs (range 0.4-15 g) using the up-down paradigm (Chaplan et al., 1994), as previously described (Ekberg et al., 2006). The maximum possible score (15 g) was recorded when animals failed to respond to the 15 g von Frey hair. Pre-surgery baseline thresholds were 14.7±0.3 g (n=21). The experimenter was blinded to all drug treatments. Catheter patency and placement were confirmed after all experiments by postmortem visualization of the spread of a second intrathecal methylene blue injection (10 ml, 4%) over the lumbar enlargement.

Figure 10:
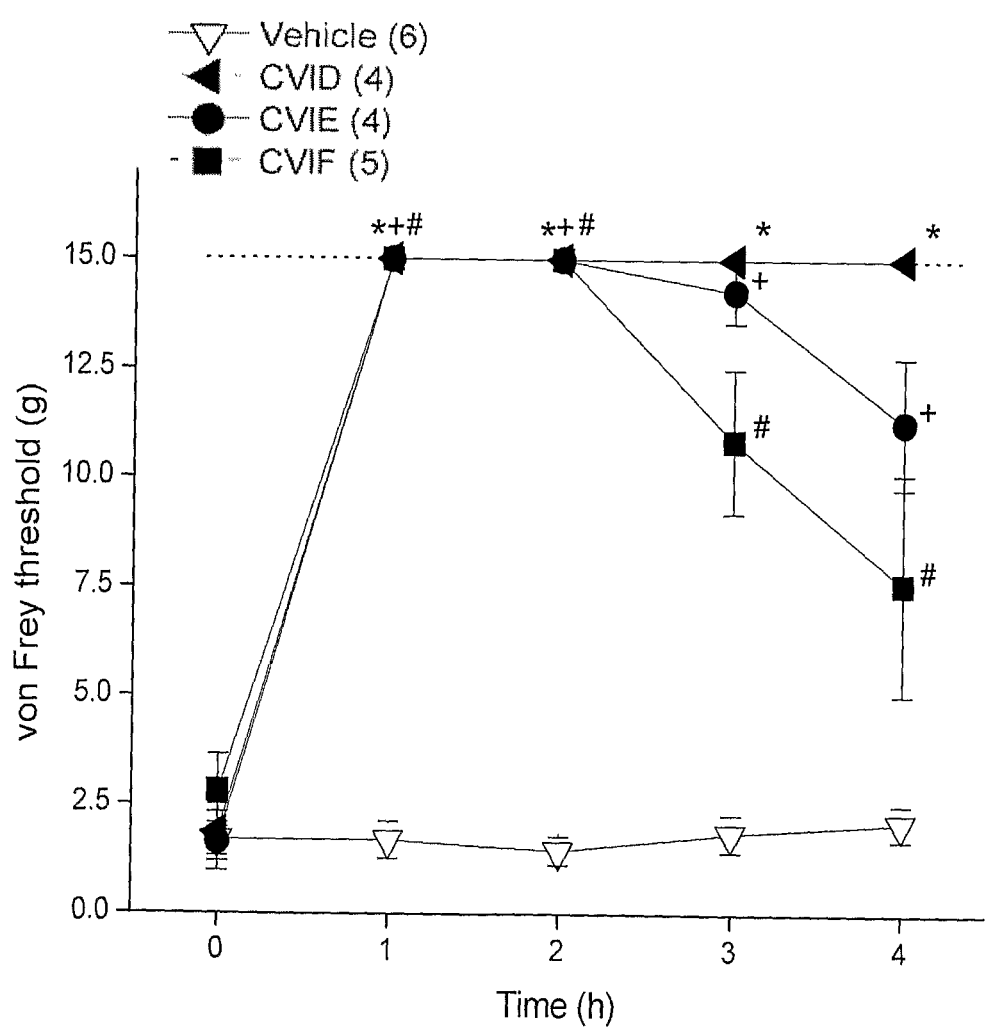
FIG. 10 shows that intrathecal injection of 1 nM ω-conotoxin CVID, CVIE or CVIF but not saline vehicle (10 µl) completely relieves mechanical allodynia in a nerve injury model of neuropathic pain for up to 4 hours after injection.
Figure 11:
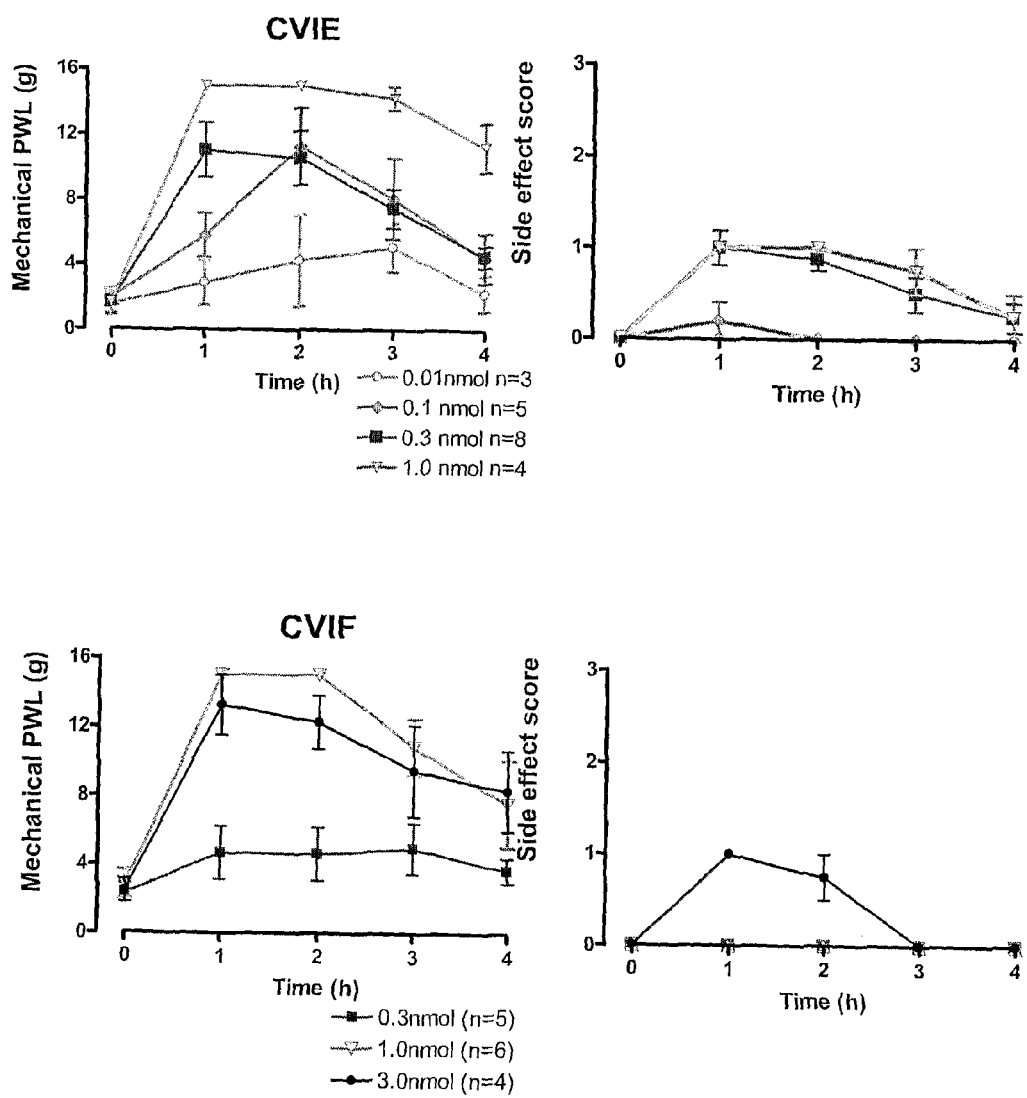
FIG. 11 shows the effect that application of different concentrations of CVIE and CVIF has on mechanical allodynia in a nerve injury model of neuropathic pain, and the comparative amount of side effects observed at each of these concentrations.
Figure 12:
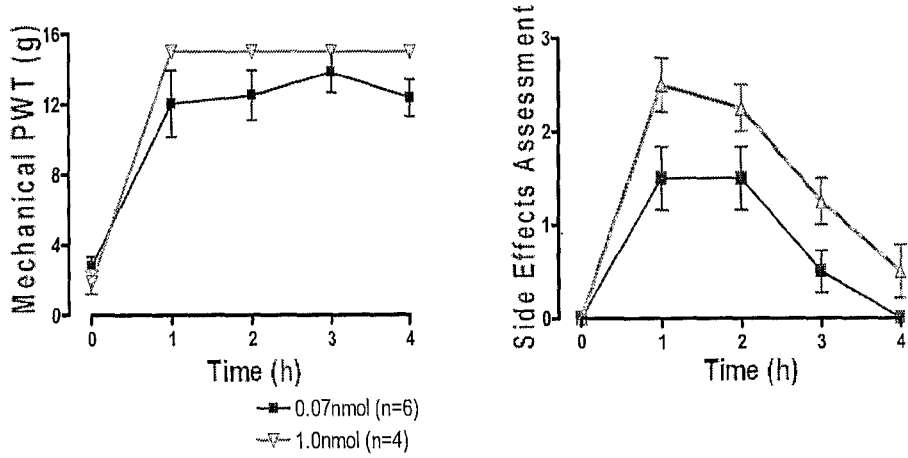
FIG. 12 shows the effect that application of different concentrations of CVID, CVIF and [R10K]CVIF has on mechanical allodynia in a nerve injury model of neuropathic pain, and the comparative amount of side effects observed at these concentrations.
Figure 12:
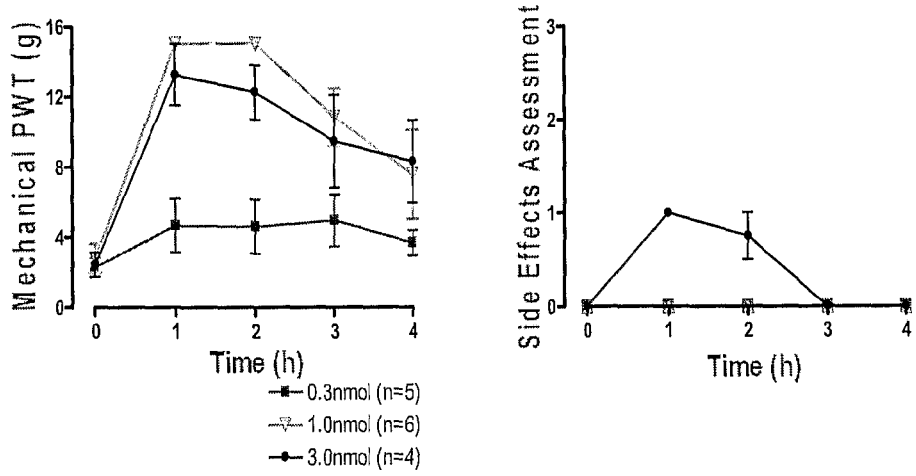
Figure 12:
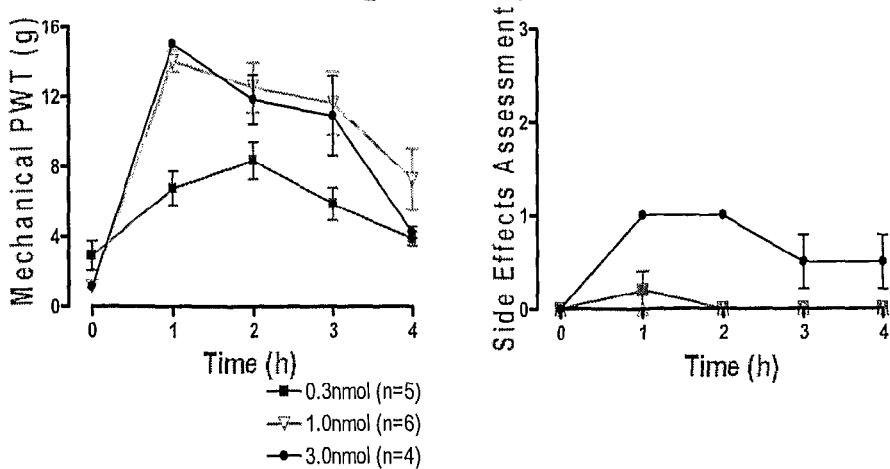
Figure 13:
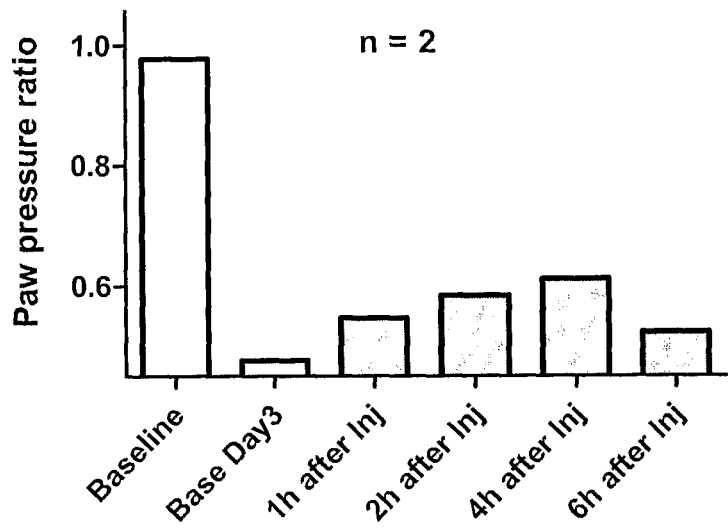
FIG. 13 shows the effect of subcutaneous administration of CVID (A) and saline (B) on the weight bearing ability of the paw of mice with mechanical allodynia.
Figure 13:
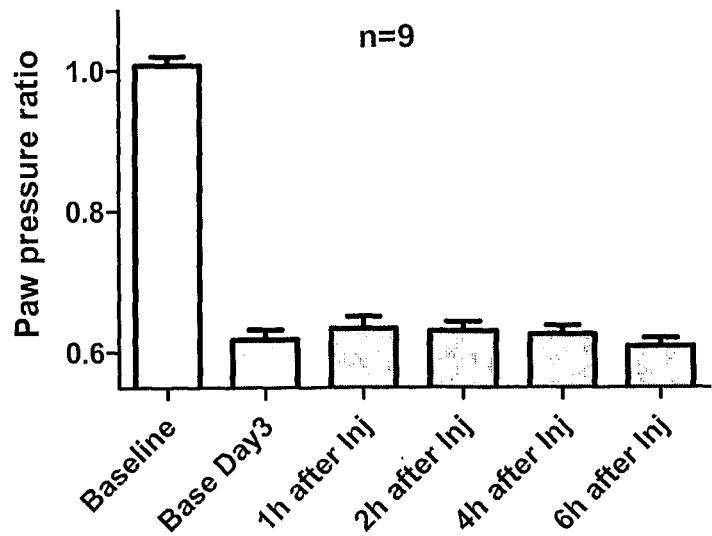
Figure 14:
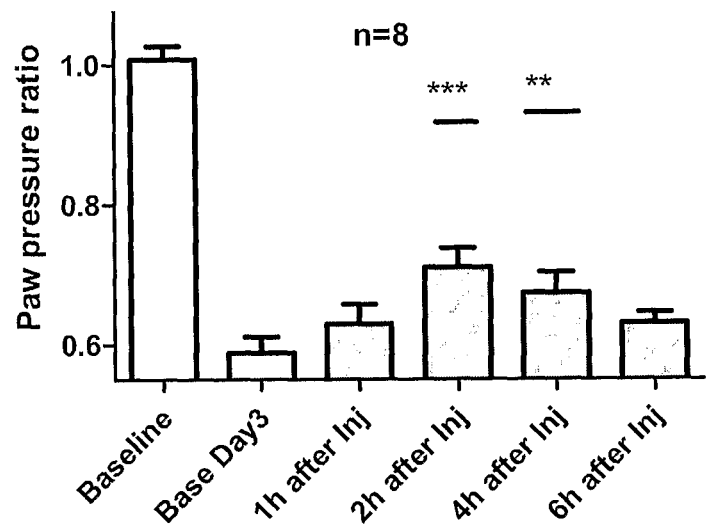
FIG. 14 shows the effect of subcutaneous administration of CVIE (A) and [R10K]CVIE (B) on the weight bearing ability of the paw of mice with mechanical allodynia.
Figure 14:
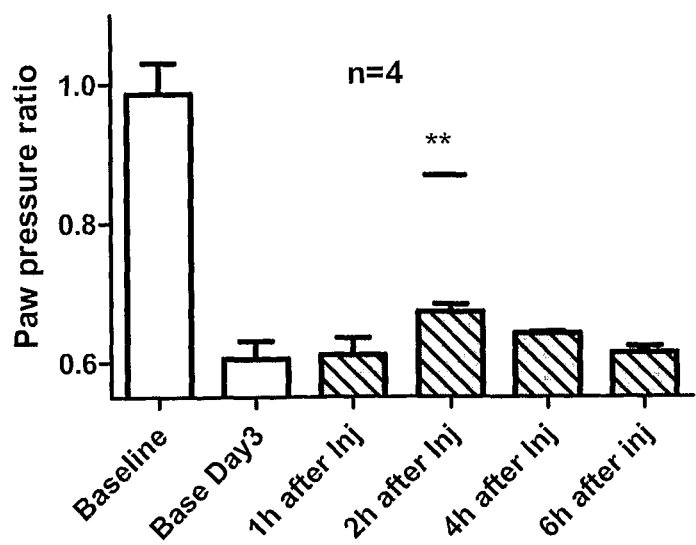
Figure 15:
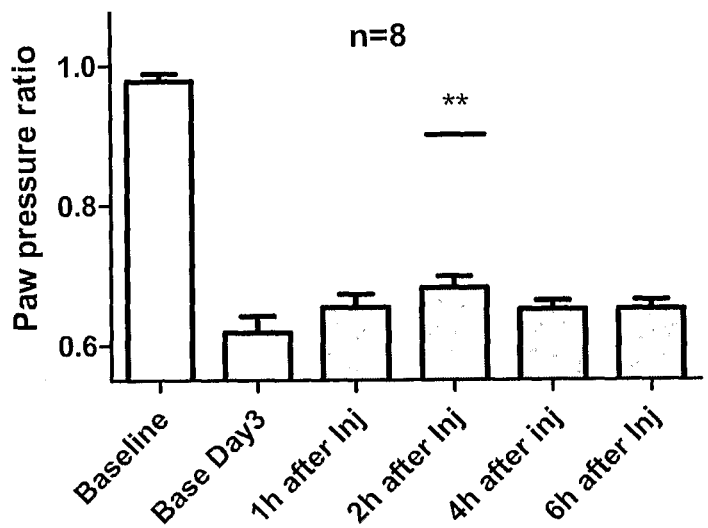
FIG. 15 shows the effect of subcutaneous administration of CVIF (A) and [R10K]CVIF (B) on the weight bearing ability of the paw of mice with mechanical allodynia.
Figure 15:
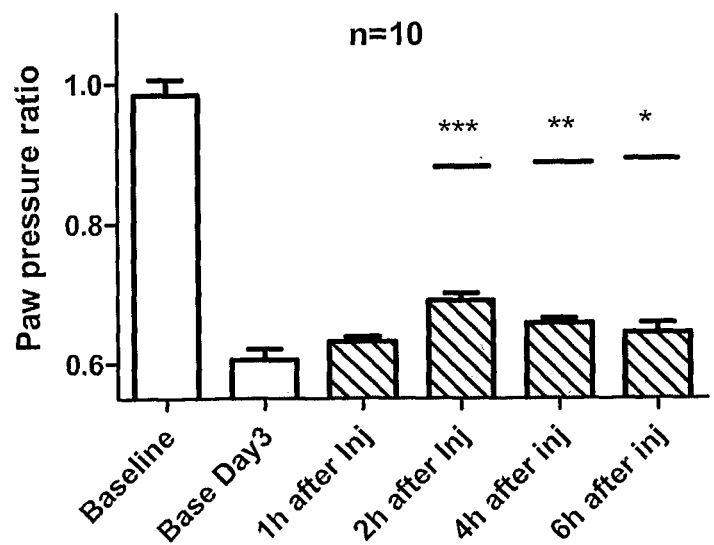

Partial nerve ligation (PNL) produced a profound reduction in paw withdrawal threshold from the pre-surgery baseline of 14.7±0.3 g (n=21), indicating the development of mechanical allodynia (FIG. 10). As shown in FIG. 10, intrathecal injection of 1 nM ω-conotoxin CVID, CVIE or CVIF but not saline vehicle (10 µl) completely relieves mechanical allodynia in a nerve injury model of neuropathic pain for up to 4 hours after injection. In the Figure, the broken line indicates pre-surgery baseline paw withdrawal threshold in the paw ipsilateral to the nerve injury and *, + and #, respectively, denote significant difference between treatment and vehicle (in all cases, p<0.001, two-way ANOVA, Bonferroni posthoc test). The numbers between parentheses indicate the number of experiments.

As reported previously for CVID (Scott et al., 2002), a dose of 1 nM of intrathecal CVID, CVIE or CVIF produced significant reversal of mechanical allodynia to pre-injury baseline levels (two-way ANOVA, $p<0.001$). As shown in FIGS. 11 and 12, CVIE, CVIF and [R10K]CVIF were also tested for their ability to relieve mechanical allodynia at different concentrations and CVID was also tested for comparison. All peptides relieved mechanical allodynia at a concentration of 1 nmol.

The side effects of each of these peptides at the concentrations tested was also assessed. All peptides produced side effects typical of ω-conotoxins, including shakes and tail twitching and serpentine tail movements, as reported previously for CVID (Scott et al., 2002). However, and as shown in FIGS. 11 and 12, CVIE, CVIF and [R10K]CVIF exhibited substantially decreased side effects compared to CVID. Moreover, CVIE, CVIF and [R10K]CVIF exhibited fewer side effects than CVID or MVIIA when tested under equivalent protocols.

Example 8

Male C57 B16 mice were purchased from ARC Perth. All mice weighed 20-25 g. The mice were housed in groups of four with ad lib access to food and water at 22±1° C. on a 12 hour light/dark cycle (light from 6 am to 6 pm, dark from 6 pm to 6 am). All mice were injected subcutaneously in the plantar surface of the left hindpaw with 50 μL undiluted Complete Freund's Adjuvant (CFA) (Sigma-Aldrich, USA) using a 50 μL Hamilton syringe. Signs of inflammatory pain typically develop within 24 hours of injection using this procedure in mice. Signs of mechanical allodynia are maximal 3-4 days after injection and decline slowly over more than one week.

The severity of mechanical allodynia was measured using an incapacitance test that employed an automated device (the Linton Incapacitance Tester, Linton Instruments) to simultaneously determine weight load on each hindpaw while the mouse is enclosed in a holder designed to allow some free movement but favour placing hindpaws on the pressure sensor. The instrument provides a numerical readout of load on each paw in grams. At each time point five measurements are collected over 3-5 minutes while the mouse is resting with both paws appropriately located on the pressure sensors. The five measurements are averaged and the ratio of load on left/right paw recorded as a single data point. This incapacitance test is responsive to pain relieving drugs.

Inflammatory pain signs were scored by a trained observer familiar with the procedures of the experiment but blinded to the drug treatments administered. Prior to induction of chronic inflammatory pain all mice were scored for incapacitance. Because weight load on each paw is usually balanced at rest, the ratio scores are close to a value of 1 (see FIGS. 13 to 15). Three days after induction of inflammatory pain the load placed on the inflamed paw is dramatically reduced. This is clear in all cases with the usual ratios being approximately 0.6 for left/right paw.

On the day of the experiment an aliquot of each peptide, stored in stock solution at −30° C., was thawed by an independent researcher and then prepared in sterile, pyrogen free isotonic saline (0.9%) to a concentration of 2 mg/10 ml. In all mice a baseline measure of incapactiance was recorded immediately before drug injection (3 days after pain induction). At time zero on the day of drug testing blinded drugs or vehicle (sterile isotonic saline) were injected by the observer subcutaneously near the scruff of the neck in a volume of 10 ml/kg. Each syringe used contained no more than 2 coded doses (sometimes 1) and most daily experiments included 8 animals.

Three animals were rejected from further analysis because they displayed unusual behaviours (tail writhing) and did not produce robust incapacitance responses. It was later found that these animals had been administered saline, and data from these animals were not included in the data sets.

Data for each treatment were collated and analysed using GraphPad Prism version 5. Data were analyzed by one-way ANOVA for each treatment with repeated measures and, when significant, Dunnett's post-hoc tests for planned contrasts between baseline on day of injection and each post-drug time.

Incapacitance scores were recorded for each animal at 1, 2, 4, and 6 hours after injection with CVID (FIG. 13A, 2 animals), saline (FIG. 13B, 9 animals), CVIE (FIG. 14A, 8 animals), [R10K]CVIE (FIG. 14B, 4 animals), CVIF (FIG. 15A, 8 animals) and [R10K]CVIF (FIG. 15B, 10 animals) (for all Figures *=$P<0.05$; =$P<0.01$; *=$P<0.001$).

CVIE produced highly significant reversal of incapacitance at 2 hours ($P<0.001$) and 4 hours after injection ($P<0.01$) and this had subsided by 6 hours (FIG. 14A). [R10K]CVIE produced significant reversal of incapacitance at 2 hours ($P<0.01$) and this had subsided by 4 and 6 hours (FIG. 14B). CVIF produced significant reversal of incapacitance at 2 hours ($P<0.01$) and this had subsided by 4 and 6 hours (FIG. 15A). [R10K]CVIF produced highly significant reversal of incapacitance at 2 hours ($P<0.001$) and this was sustained at 4 hours ($P<0.01$) and 6 hours ($P<0.05$) after injection (FIG. 15B). Throughout the experiments saline had no effect (FIG. 13B).

Omega conotoxins often produce characteristic side effect signs in rodents after intrathecal injection. These include tail writhing, paw tremor and whole body shakes. All animals were observed individually for these signs and another observable signs such as obvious sedation of hyperactivity, any form of shaking, display of discomfort including piloerection and escape behaviour. These were scored for each animal in an observation chamber for a period of 5 minutes at each time point. Only three animals in the entire experiment displayed any observable sign, tail shaking (that disturbed incapacitance measurements), but these were all subsequently found to have been injected with vehicle only. These animals were not included in the analysis.

REFERENCES

Australian Patent Application No. 2006236006.
Bettler et al., (2004) *Physiological Reviews* 84: 835-867.
Bowery et al., (2002) *Pharmacological Reviews* 54: 247-264.
Brock J and Cunnane T C (1987) Relationship between the nerve action potential and transmitter release from sympathetic postganglionic nerve terminals. *Nature* 326: 605-607.
Bures et al., (1998) *Biochemistry* 37: 12172-7.
Butler, M. ed. (1991) Mammalian Cell Biotechnology: A Practical Approach, IRL Press.
Chaplan S R, Bach F W, Pogrel J W, Chung J M and Yaksh T L (1994) Quantitative assessment of tactile allodynia in the rat paw. *J Neurosci Methods* 53: 55-63.
Cleland et al., (1993) *Crit. Rev. Therap. Drug Carr, Syst.,* 10: 307-366.
Ekberg J, Jayamanne A, Vaughan C W, Aslan S, Thomas L, Mould J, Drinkwater R, Baker M D, Abrahamsen B, Wood J N, Adams D J, Christie M J and Lewis R J (2006) µO-conotoxin MrVIB selectively blocks Nav1.8 sensory neuron specific sodium channels and chronic pain behavior without motor deficits. *Proc Natl Acad Sci USA* 103: 17030-17035.
Flinn et al. (1995), *J Pept Sci* 1: 379-84.
Hamill O P, Marty A, Neher E, Sakmann B and Sigworth F J (1981) Improved patch-clamp techniques for high-resolution current recording from cells and cell-free membrane patches. *Pflugers Arch.* 391:85-100.
Hile, Courtney and Dum, 1975, In *Molecular Mechanisms of Anesthesia*, Vol. 1: Prog. In Anesthesiology, B R Fink (ed.) Raven Press, NY 13-20.
Kent et al. (1998) *Biopolymers* 46: 53-63.
Lew et al. (1997) *J Biol Chem* 272: 12014-23.
Lewis R J, Nielsen K J, Craik D J, Loughnan M L, Adams D A, Sharpe I A, Luchian T, Adams D J, Bond T, Thomas L, Jones A, Matheson J L, Drinkwater R, Andrews P R and Alewood P F (2000) Novel ω-conotoxins from *Conus catus* discriminate among neuronal calcium channel subtypes. *J Biol Chem* 275: 35335-35344.
Moffatt F, Senkans P and Ricketts D (2000) Approaches towards the quantitative analysis of peptides and proteins by reversed-phase high-performance liquid chromatography in the absence of a pure reference sample. *J Chromatogr A* 891: 235-242.
Motin L and Adams D J (2008) ω-conotoxin inhibition of excitatory synaptic transmission evoked by dorsal root stimulation in rat superficial dorsal horn. *Neuropharmacology* 55: 860-864.
Motin L, Yasuda T, Schroeder C I, Lewis R J and Adams D J (2007) ω-conotoxin CVIB differentially inhibits native and recombinant N- and P/Q-type calcium channels. *Eur J Neurosci* 25: 435-444.
Mould J, Yasuda T, Schroeder C I, Beedle A M, Doering C J, Zamponi G W, Adams D J and Lewis R J (2004) The $\alpha_2\delta$ auxiliary subunit reduces affinity of ω-conotoxins for recombinant N-type ($Ca_v2.2$) calcium channels. *J Biol Chem* 279: 34705-34714.
Neumann et al., (1999) *British Journal of Pharmacology* 128: 1623-1629.
Purves R D (1991) Microelectrode methods for intracellular recording and ionophoresis, Academic Press, Harcourt Brace Jovanovich Publishers.
Sambrook et al. (1989) Molecular Cloning: A Laboratory Manual, Cold Spring Harbor Laboratory Press.
Sato et al. (1991) *J Biol Chem* 266: 16989-91.
Shon et al., (1997) *Biochemistry* 36: 9581-7.
Schnolzer M, Alewood P, Jones A, Alewood D and Kent S B (1992) In situ neutralization in Boc-chemistry solid phase peptide synthesis. Rapid, high yield assembly of difficult sequences. *Int J Pept Protein Res* 40: 180-193.
Scott D A, Wright C E and Angus J A (2002) Actions of intrathecal ω-conotoxins CVID, GVIA, MVIIA, and morphine in acute and neuropathic pain in the rat. *Eur J Pharmacol* 451: 279-286.
Seltzer Z, Dubner R and Shir Y (1990) A novel behavioral model of neuropathic pain disorders produced in rats by partial sciatic nerve injury. *Pain* 43: 205-218.
Smith A B and Cunnane T C (1997) Multiple calcium channels control neurotransmitter release from rat postganglionic sympathetic nerve terminals. *J. Physiol.* 499:341-349.
Smith A B and Cunnane T C (1996) Ryanodine-sensitive calcium stores involved in neurotransmitter release from sympathetic nerve terminals of the guinea-pig. *J. Physiol.* 497:657-664.
Stocker J W, Nadasdi L, Aldrich R W and Tsien R W (1997) *J Neurosci* 17, 3002-3013.
U.S. Pat. No. 4,569,967.
Yasuda T, Lewis R J and Adams D J (2004) Overexpressed $Ca_v\beta3$ inhibits N-type ($Ca_v2.2$) calcium channel currents through a hyperpolarizing shift of ultra-slow and closed-state inactivation. *J Gen Physiol* 123: 401-416.
WO 91/07980.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The claims defining the invention are as follows:

1. An isolated, synthetic or recombinant peptide, wherein the peptide comprises the sequence:

SEQ ID NO: 1
CKGKGAXaa$_1$CRXaa$_2$Xaa$_3$Xaa$_4$YXaa$_5$CCXaa$_6$GXaa$_7$CRXaa$_8$Xaa$_9$RC wherein
Xaa$_1$, Xaa$_3$, Xaa$_4$, Xaa$_6$, Xaa$_7$ and Xaa$_8$ are independently selected from serine and threonine;
Xaa$_2$ is selected from arginine and lysine;
Xaa$_5$ is selected from aspartic acid and glutamic acid;
Xaa$_9$ is selected from glycine, alanine, valine, leucine and isoleucine; and
wherein the C-terminal cysteine of SEQ ID NO:1 is a carboxyl group, primary amide or linked to the N-terminus by a linker.

2. The isolated, synthetic or recombinant peptide according to claim 1, wherein Xaa$_9$ is selected from glycine, alanine, leucine or isoleucine.

3. The isolated, synthetic or recombinant peptide according to claim 1, wherein Xaa$_9$ is glycine.

4. The isolated, synthetic or recombinant peptide according to claim 1, wherein Xaa$_9$ is leucine.

5. The isolated, synthetic or recombinant peptide according to claim 1, wherein Xaa$_2$ is arginine.

6. The isolated, synthetic or recombinant peptide according to claim 1, wherein Xaa$_2$ is lysine.

7. The isolated, synthetic or recombinant peptide according to claim 1, wherein Xaa$_1$, Xaa$_4$, Xaa$_7$ and Xaa$_8$ are each serine, Xaa$_3$ and Xaa$_6$ are each threonine and Xaa$_5$ is aspartic acid.

8. The isolated, synthetic or recombinant peptide according to claim 1, wherein the peptide is selected from:

SEQ ID NO: 2
C K G K G A S C R R T S Y D C C T G S C R S L R C

SEQ ID NO: 3
C K G K G A S C R K T S Y D C C T G S C R S L R C

SEQ ID NO: 4
C K G K G A S C R R T S Y D C C T G S C R S G R C
and

SEQ ID NO: 5
C K G K G A S C R K T S Y D C C T G S C R S G R C.

9. The isolated, synthetic or recombinant peptide according to claim 1, wherein the six cysteine residues in SEQ ID NO: 1 are bonded in pairs to form three cysteine-cysteine bonds.

10. The isolated, synthetic or recombinant peptide according to claim 9, wherein the cysteine-cysteine bonds in SEQ ID NO: 1 are: C1-C16; C8-C20; and C15-C25, numbered from the N-terminus.

11. The isolated, synthetic or recombinant peptide according claim 10, wherein one or more of the cysteine-cysteine bonds form diselenide bonds.

12. The isolated, synthetic or recombinant peptide according to claim 1, wherein the C-terminus of the peptide is a primary amide.

13. The isolated, synthetic or recombinant peptide according to claim 1, wherein the C-terminus of the peptide is a primary amide and the N-terminus is a primary amine.

14. The isolated, synthetic or recombinant peptide according to claim 1, wherein at least one of the amino acids incorporates a radiolabel or a fluorescent label.

15. A composition comprising a peptide according to claim 1, and a pharmaceutically acceptable carrier or diluent.

* * * * *

SEQUENCE LISTING

<160> NUMBER OF SEQ ID NOS: 5

<210> SEQ ID NO 1
<211> LENGTH: 25
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa is selected from serine and threonine
<220> FEATURE:
<221> NAME/KEY: MISC_FEATURE
<222> LOCATION: (10)..(10)
<223> OTHER INFORMATION: Xaa is selected from arginine and lysine
<220> FEATURE:
<221> NAME/KEY: MISC_FEATURE
<222> LOCATION: (11)..(11)
<223> OTHER INFORMATION: Xaa is selected from serine and threonine
<220> FEATURE:
<221> NAME/KEY: MISC_FEATURE
<222> LOCATION: (12)..(12)
<223> OTHER INFORMATION: Xaa is selected from serine and threonine
<220> FEATURE:
<221> NAME/KEY: MISC_FEATURE
<222> LOCATION: (14)..(14)
<223> OTHER INFORMATION: Xaa is selected from aspartic acid and glutamic
      acid
<220> FEATURE:
<221> NAME/KEY: MISC_FEATURE
<222> LOCATION: (17)..(17)
<223> OTHER INFORMATION: Xaa is selected from serine and threonine
<220> FEATURE:
<221> NAME/KEY: MISC_FEATURE
<222> LOCATION: (19)..(19)
<223> OTHER INFORMATION: Xaa is selected from serine and threonine
<220> FEATURE:
<221> NAME/KEY: MISC_FEATURE
<222> LOCATION: (22)..(22)
<223> OTHER INFORMATION: Xaa is selected from serine and threonine
<220> FEATURE:
<221> NAME/KEY: MISC_FEATURE
<222> LOCATION: (23)..(23)
<223> OTHER INFORMATION: Xaa is selected from glycine, alanine, valine,
      leucine, and isoleucine

<400> SEQUENCE: 1

Cys Lys Gly Lys Gly Ala Xaa Cys Arg Xaa Xaa Xaa Tyr Xaa Cys Cys
1               5                   10                  15

Xaa Gly Xaa Cys Arg Xaa Xaa Arg Cys
            20                  25

<210> SEQ ID NO 2
<211> LENGTH: 25
<212> TYPE: PRT
<213> ORGANISM: Conus catus

<400> SEQUENCE: 2

Cys Lys Gly Lys Gly Ala Ser Cys Arg Arg Thr Ser Tyr Asp Cys Cys
1               5                   10                  15

Thr Gly Ser Cys Arg Ser Leu Arg Cys
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Cys Lys Gly Lys Gly Ala Ser Cys Arg Lys Thr Ser Tyr Asp Cys Cys
1               5                   10                  15

Thr Gly Ser Cys Arg Ser Leu Arg Cys
            20                  25
```

```
<210> SEQ ID NO 4
<211> LENGTH: 25
<212> TYPE: PRT
<213> ORGANISM: Conus catus

<400> SEQUENCE: 4

Cys Lys Gly Lys Gly Ala Ser Cys Arg Arg Thr Ser Tyr Asp Cys Cys
1               5                   10                  15

Thr Gly Ser Cys Arg Ser Gly Arg Cys
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic [R10K]CVIE

<400> SEQUENCE: 5

Cys Lys Gly Lys Gly Ala Ser Cys Arg Lys Thr Ser Tyr Asp Cys Cys
1               5                   10                  15

Thr Gly Ser Cys Arg Ser Gly Arg Cys
            20                  25
```